United States Patent
Mouneimne et al.

(10) Patent No.: US 12,351,877 B2
(45) Date of Patent: Jul. 8, 2025

(54) SYSTEMS AND METHODS FOR DETERMINING A TREATMENT COURSE OF ACTION

(71) Applicant: Arizona Board of Regents on Behalf of the University of Arizona, Tucson, AZ (US)

(72) Inventors: Ghassan Mouneimne, Tucson, AZ (US); Marco Padilla-Rodriguez, Tucson, AZ (US)

(73) Assignee: Arizona Board of Regents on Behalf of the University of Arizona, Tucson, AZ (US)

( * ) Notice: Subject to any disclaimer, the term of this patent is extended or adjusted under 35 U.S.C. 154(b) by 772 days.

(21) Appl. No.: 17/253,690

(22) PCT Filed: Jun. 21, 2019

(86) PCT No.: PCT/US2019/038433
§ 371 (c)(1),
(2) Date: Dec. 18, 2020

(87) PCT Pub. No.: WO2019/246499
PCT Pub. Date: Dec. 26, 2019

(65) Prior Publication Data
US 2021/0198753 A1    Jul. 1, 2021

Related U.S. Application Data

(60) Provisional application No. 62/688,156, filed on Jun. 21, 2018.

(51) Int. Cl.
| | |
|---|---|
| *C12Q 1/6886* | (2018.01) |
| *A61K 31/015* | (2006.01) |
| *A61K 31/10* | (2006.01) |
| *A61K 31/138* | (2006.01) |
| *A61K 31/4196* | (2006.01) |
| *A61K 45/06* | (2006.01) |
| *G01N 33/574* | (2006.01) |

(52) U.S. Cl.
CPC .......... *C12Q 1/6886* (2013.01); *A61K 31/015* (2013.01); *A61K 31/10* (2013.01); *A61K 31/138* (2013.01); *A61K 31/4196* (2013.01); *A61K 45/06* (2013.01); *G01N 33/57484* (2013.01); *C12Q 2600/106* (2013.01); *C12Q 2600/158* (2013.01); *G01N 2333/723* (2013.01)

(58) Field of Classification Search
CPC .......... C12Q 1/6886; C12Q 2600/158; C12Q 2600/106; G01N 33/57484; A61K 31/015; A61K 31/10; A61K 31/138; A61K 31/4196; A61K 45/06; A61K 31/565; A61K 31/5685; A61P 19/04
See application file for complete search history.

(56) References Cited

U.S. PATENT DOCUMENTS

| | | |
|---|---|---|
| 5,225,326 A | 7/1993 | Bresser et al. |
| 5,545,524 A | 8/1996 | Trent |
| 6,121,489 A | 9/2000 | Dorner et al. |
| 6,573,043 B1 | 6/2003 | Cohen et al. |
| 6,690,976 B2 | 2/2004 | Fenn et al. |
| 8,658,396 B2 | 2/2014 | Turner et al. |
| 2003/0219767 A1* | 11/2003 | Ayers .............. C12Q 1/6886 435/6.14 |
| 2004/0058340 A1* | 3/2004 | Dai ................ C12Q 1/6886 435/6.12 |
| 2008/0193938 A1* | 8/2008 | Kun ................ C12Q 1/6886 506/17 |

FOREIGN PATENT DOCUMENTS

| | | |
|---|---|---|
| WO | WO 2009/100161 | 8/2009 |
| WO | WO 2011/019074 | 2/2011 |

OTHER PUBLICATIONS

NCBI Gene entry for EVL, available from https://www.ncbi.nlm.nih.gov/gene/51466, updated Oct. 15, 2023, printed as pp. 1/8-8/8; e.g., p. 1. (Year: 2023).*
Hormone Therapy for Breast Cancer, published by the National Cancer Institute. Available from https://www.cancer.gov/types/breast/breast-hormone-therapy-fact-sheet on Jan. 20, 2017, printed as p. 1/4-4/4. (Year: 2017).*
Jordan et al. New hypotheses and opportunities in endocrine therapy: amplification of oestrogen-induced apoptosis. The Breast, vol. 18, vol. S3, pp. S10-S17, 2009. (Year: 2009).*
Jordan, VC. The 38th David A. Karnofsky Lecture: The Paradoxical Actions of Estrogen in Breast Cancer—Survival or Death? Journal of Clinical Oncology, vol. 26, pp. 3073-3082, Jun. 20, 2008. (Year: 2008).*
Kai et al. Force matters: Biomechanical regulation of cell invasion and migration in disease. Trends in Cell Biology, vol. 25, No. 7, pp. 486-497, Jul. 2016. (Year: 2016).*
Barcus et al. Dense collagen-I matrices enhance pro-tumorigenic estrogen-prolactin crosstalk in MCF-7 and T47D breast cancer cells. PLoS ONE, vol. 10, No. 1, e0116891, Jan. 21, 2015; printed as pp. 1/22-22/22. (Year: 2015).*
Reinert et al. Multidisciplinary approach to neoadjuvant endocrine therapy in breast cancer: A comprehensive review. Revista brasileira de ginecologia e obstetrícia : revista da Federação Brasileira das Sociedades de Ginecologia e Obstetrícia. vol. 38, No. 12, pp. 615-622, Dec. 2016. (Year: 2016).*
Fischer et al. Hematoxylin and eosin staining of tissue and cell sections. CSH Protocols, vol. 3, No. 5, pp. 1-3, May 2008. (Year: 2008).*
Entry for "estrogen receptor negative" in the NCI Dictionary of Cancer Terms. https://www.cancer.gov/publications/dictionaries/cancer-terms/def/estrogen-receptor-negative, printed as p. 1/1, publicly available Feb. 6, 2018 (Year: 2018).*

(Continued)

*Primary Examiner* — Sarae L Bausch
(74) *Attorney, Agent, or Firm* — Casimir Jones, S.C.; Tanya A. Arenson

(57) ABSTRACT

The present disclosure relates to methods of determining a treatment course of action. In particular, the present disclosure relates to compositions and methods for determining responsiveness to estrogen and estrogen blocking therapies for cancer.

7 Claims, 29 Drawing Sheets

Specification includes a Sequence Listing.

(56) References Cited

OTHER PUBLICATIONS

Hasebe et al. Fibrotic focus in invasive ductal carcinoma: An indicator of high tumor aggressiveness. Japanese Journal of Cancer Research, vol. 87, pp. 385-394, Apr. 1996. (Year: 1996).*
Cizeron-Clairac et al. BMC Cancer (2015) 15:499, pp. 1-14.*
Bastarrachea et al., Annals of Internal Medicine, 120: 18 [1994].
Behbod, F. et al. Breast Cancer Res. 11, R66 (2009).
Bonnier, P. et al. International Journal of Cancer 79, 278-282 (1998).
Branton et al., Nat. Biotechnol. 26(10):1146-53 (2008).
Bravo-Cordero et al. Curr. Opin. Cell Biol. 24, 277-283 (2012).
Cancer Genome Atlas Network. Nature 490, 61-70 (2012).
Carroll, J. S. et al. Cell 122, 33-43 (2005).
Chou, Y.-Y. et al. Identification and Characterization of a Novel Broad-Spectrum Virus Entry Inhibitor. J. Virol. 90, 4494-4510 (2016).
Ginestier, C. et al. Clinical Cancer Research 12, 4533-4544 (2006).
Curtis, C. et al. Nature 486, 346-352 (2012).
Cutuli, B. et al. Breast Cancer Res Treat 95, 55-64 (2006).
Delgado, R. C. & Lubian Lopez, D. M. Maturitas 38, 147-156 (2001).
Drmanac, et al., Nat. Biotechnol. 16:54-58 (1998).
Edwards et al., Journal of Clinical Oncology 16: 2693 [1998].
Eid et al., Science 323:133-138 (2009).
Elledge et al., Journal of the National Cancer Institute 86: 705 [1994].
Esserman, L. J. et al. Breast Cancer Res Treat 132, 1049-1062 (2012).
Fischer, R. S., et al., Curr. Biol. 19, 260-265 (2009).
Gao, Y. et al. Nature Communications 8, 14483 (2017).
Gatrell, A. C., et al. Transactions of the Institute of British Geographers 21, 256 (1996).
Giretti et al. Rapid regulatory actions of sex steroids on cell movement through the actin cytoskeleton, Steroids, 2008, vol. 73, pp. 895-900.
Gluck, S. et al. Breast Cancer Res Treat 132, 781-791 (2012).
Haque, R. et al. Biomarkers Prev. 21, 1848-1855 (2012).
Harris et al., Science 320:106-109 (2008).
International Search Report & Written Opinion, International Patent Application No. PCT/US2019/038433, mailed Sep. 24, 2019, 13 pages.
Kanchanawong, P. et al. Nature 468, 580-584 (2010).
Kao, K.-J., et al. BMC Cancer 11, 143 (2011).
Kato, Int. J. Clin. Exp. Med. 2:193-202 (2009).
Klinger, et al., Am. J. Hum. Genet. 51:55-65 (1992).
Korde, L. A. et al. Breast Cancer Res Treat 119, 685-699 (2010).
Korlach et al., Proc. Natl. Acad. Sci. USA 105:1176-1181 (2008).
Kuo, et al., Am. J. Hum. Genet. 49:112-119 (1991).
Levene et al., Science 299:682-686 (2003).
Lomakin, A. J. et al. Nat. Cell Biol. 17, 1435-1445 (2015).
Lu, X. et al. Breast Cancer Res Treat 108, 191-201 (2008).
Maclean et al., Nature Rev. Microbiol., Apr. 2009, 7: 287-296.
Margulies et al., Nature 437:376-380 (2005).
Maxam et al., Proc. Natl. Acad. Sci. USA 74:560-564 (1977).
Meyer, A. S. et al. J. Cell Biol. 197, 721-729 (2012).
Miyake, T. et al. Cancer Sci. 103, 913-920 (2012).
Mouneimne, G. et al. Differential remodeling of actin cytoskeleton architecture by profilin isoforms leads to distinct effects on cell migration and invasion. Cancer Cell 22, 615-630 (2012).
The BAC Resource Consortium, Integration of cytogenetic landmarks into the draft sequence of the human genome, Nature 409: 953-958 (2001).
Obi, N. et al. International Journal of Cancer 138, 2098-2108 (2016).
Platet, N., et al. Crit. Rev. Oncol. Hematol. 51, 55-67 (2004).
Rauh, C. et al. Geburtshilfe Frauenheilkd 75, 588-596 (2015).
Richardson, A. L. et al. Cancer Cell 9, 121-132 (2006).
Ronaghi et al., Anal. Biochem. 242:84-89 (1996).
Ruparel et al., Proc. Natl. Acad. Sci. USA 102:5932-5937 (2005).
Sacchini, V. et al. Ann. Surg. Oncol. 9, 266-271 (2002).
Sage, D. et al. Quantitative evaluation of software packages for single-molecule localization microscopy. Nat. Methods 12, 717-724 (2015).
Sanger et al., Proc. Natl. Acad. Sci. USA 74:5463-5467 (1997).
Schuetz, F. et al. American Journal of Obstetrics and Gynecology 196, 342.e1-342.e9 (2007).
Sflomos, G. et al. A Preclinical Model for ERα-Positive Breast Cancer Points to the Epithelial Microenvironment as Determinant of Luminal Phenotype and Hormone Response. Cancer Cell 29, 407-422 (2016).
Shtengel, G. et al. Interferometric fluorescent super-resolution microscopy resolves 3D cellular ultrastructure. Proc. Natl. Acad. Sci. U.S.A. 106, 3125-3130 (2009).
Stickeler, E. et al. Oncol. Rep. 26, 1037-1045 (2011).
Vicente-Manzanares et al., J. Cell Biol. 176, 573-580 (2007).
Vidya, R. BMJ 321, 179-179 (2000).
Voelkerding et al., Clinical Chem., 55: 641-658, 2009.
Ward, et al., Am. J. Hum. Genet. 52:854-865 (1993).

\* cited by examiner

SEQUENCE LISTING

```
<160> NUMBER OF SEQ ID NOS: 4

<210> SEQ ID NO 1
<211> LENGTH: 21
<212> TYPE: DNA
<213> ORGANISM: Artificial sequence
<220> FEATURE:
<223> OTHER INFORMATION: synthetic

<400> SEQUENCE: 1
tactaggatc ttccatttgg c                                              21

<210> SEQ ID NO 2
<211> LENGTH: 19
<212> TYPE: DNA
<213> ORGANISM: Artificial sequence
```

```
<220> FEATURE:
<223> OTHER INFORMATION: Synthetic

<400> SEQUENCE: 2
tggctttcat cttccttct                                                    19

<210> SEQ ID NO 3
<211> LENGTH: 9
<212> TYPE: PRT
<213> ORGANISM: Artificial sequence
<220> FEATURE:
<223> OTHER INFORMATION: Synthetic

<400> SEQUENCE: 3

Gly Gly Ser Gly Gly Ser Gly Gly Ser
1               5

<210> SEQ ID NO 4
<211> LENGTH: 20
<212> TYPE: DNA
<213> ORGANISM: Artificial sequence
<220> FEATURE:
<223> OTHER INFORMATION: Synthetic

<400> SEQUENCE: 4
acttttcagc catggccaca                                                   20
```

SYSTEMS AND METHODS FOR DETERMINING A TREATMENT COURSE OF ACTION

CROSS REFERENCE TO RELATED APPLICATIONS

This application is a U.S. 371 national phase entry of International Patent Application No. PCT/US2019/038433, filed Jun. 21, 2019, which claims priority to and the benefit of U.S. Provisional Application No. 62/688,156, filed Jun. 21, 2018, which are hereby incorporated by reference in their entireties.

STATEMENT REGARDING FEDERALLY SPONSORED RESEARCH OR DEVELOPMENT

This invention was made with government support under Grant No. R01 CA196885, awarded by NIH. The government has certain rights in the invention.

FIELD OF THE INVENTION

The present disclosure relates to methods of determining and administering a treatment course of action. In particular, the present disclosure relates to compositions and methods for determining responsiveness to estrogen and estrogen blocking therapies for cancer.

BACKGROUND OF THE INVENTION

Breast cancer is the second most common form of cancer among women in the U.S., and the second leading cause of cancer deaths among women. While the 1980s saw a sharp rise in the number of new cases of breast cancer, that number now appears to have stabilized. The drop in the death rate from breast cancer is probably due to the fact that more women are having mammograms. When detected early, the chances for successful treatment of breast cancer are much improved.

Breast cancer, which is highly treatable by surgery, radiation therapy, chemotherapy, and hormonal therapy, is most often curable when detected in early stages. Mammography is the most important screening modality for the early detection of breast cancer. Breast cancer is classified into a variety of sub-types, but only a few of these affect prognosis or selection of therapy. Patient management following initial suspicion of breast cancer generally includes confirmation of the diagnosis, evaluation of stage of disease, and selection of therapy. Diagnosis may be confirmed by aspiration cytology, core needle biopsy with a stereotactic or ultrasound technique for nonpalpable lesions, or incisional or excisional biopsy. At the time the tumor tissue is surgically removed, part of it is processed for determination of estrogen-receptor (ER) and progesterone-receptor (PR) levels.

Prognosis and selection of therapy are influenced by the age of the patient, stage of the disease, pathologic characteristics of the primary tumor including the presence of tumor necrosis, ER and PR levels in the tumor tissue, HER2 overexpression status and measures of proliferative capacity, as well as by menopausal status and general health. Overweight patients may have a poorer prognosis (Bastarrachea et al., Annals of Internal Medicine, 120: 18 [1994]). Prognosis may also vary by race, with blacks, and to a lesser extent Hispanics, having a poorer prognosis than whites (Elledge et al., Journal of the National Cancer Institute 86: 705 [1994]; Edwards et al., Journal of Clinical Oncology 16: 2693 [1998]).

The three major treatments for breast cancer are surgery, radiation, and drug therapy. No treatment fits every patient, and often two or more are required. The choice is determined by many factors, including the age of the patient and menopausal status, the type of cancer (e.g., ductal vs. lobular), its stage, whether the tumor is hormone-receptive or not, and its level of invasiveness.

Breast cancer treatments are defined as local or systemic. Surgery and radiation are considered local therapies because they directly treat the tumor, breast, lymph nodes, or other specific regions. Drug treatment is called systemic therapy, because its effects are wide spread. Drug therapies include classic chemotherapy drugs, hormone blocking treatment (e.g., aromatase inhibitors, selective estrogen receptor modulators, and estrogen receptor downregulators), and monoclonal antibody treatment (e.g., against HER2). They may be used separately or, most often, in different combinations.

There is a need for additional diagnostic and treatment options, particularly treatments customized to a patient's tumor.

SUMMARY OF THE INVENTION

Estrogen promotes growth of estrogen receptor positive (ER+) breast tumors. However, examining the prognostic characteristics of breast cancer in women treated with estrogen reveals a significant decrease in tumor dissemination, indicating that estrogen may have protective effects against cancer cell invasion. Experiments described herein demonstrated that estrogen suppresses invasion of ER+ breast cancer cells by activating the transcription of the Ena/VASP protein, EVL, which promotes the generation of Suppressive Cortical Actin Bundles (SCABs) that inhibit motility dynamics, and is crucial for the ER-mediated suppression of invasion in vitro and in vivo. Despite its benefits in suppressing tumor growth, anti-estrogenic endocrine therapy was associated with decreased EVL expression and increased local invasion. The results highlight the dichotomous effects of estrogen on tumor progression and indicate that, in contrast to its established role in promoting growth of ER+ tumors, estrogen has a significant role in suppressing invasion through EVL-mediated actin cytoskeletal remodeling. Thus, in some embodiments, provided herein are compositions and methods for treating cancer based on the level of EVL or related ER targets in cancer (e.g., breast cancer).

For example, in some embodiments, provided herein is a method of treating cancer, comprising: a) assaying a sample from a subject diagnosed with cancer for the level of expression of Enah/Vasp-Like gene (EVL) and optionally estrogen receptor; and b) administering anti-estrogen therapy when the level of expression of EVL is lower than a reference level and not administering anti-estrogen therapy when the level of expression of EVL is higher than the reference level. In some embodiments, subjects with low levels of EVL receive therapy that raises the level of EVL (e.g., estrogen). In some embodiments, estrogen is give after or before anti-estrogen therapy. In some embodiments, estrogen is given to subjects that do not respond (e.g., do not exhibit a decrease in tumor size or spread or stasis of tumor size or spread) to anti-estrogen therapy. In some embodiments, the methods further comprises measuring the level of fibrosis of cancer cells. In some embodiments, subjects with high levels of fibrosis (e.g., levels of EVL above a threshold level) are administered anti-estrogen therapy.

In some embodiments, provided herein is a method of treating cancer, comprising: a) assaying a sample from a subject diagnosed with cancer for the level of expression of a tumor marker selected from, for example, EVL, TMSB15B, TMSB15B, MYO10, ANLN, TNNT1, ABLIM3, FMNL2, or LIMA1 and optionally measuring the level of estrogen receptor; and b) administering anti-estrogen therapy when the level of expression of the tumor marker is lower than a reference level and not administering anti-estrogen therapy when the level of expression of said tumor marker is higher than the reference level.

Also provided is a method of treating cancer, comprising: a) assaying a sample from a subject diagnosed with cancer for the level of expression of EVL; and b) administering estrogen therapy when the level of expression of EVL is lower than a reference level.

Further embodiments provide a method of promoting formation of SCABs in a breast tumor, comprising: a) administering estrogen to a subject that has a level of expression of EVL in the breast tumor lower than a reference level.

Yet other embodiments provide a method of recommending a cancer treatment, comprising: assaying a sample from a subject diagnosed with cancer for the level of expression of a tumor marker selected from, for example, of EVL, TMSB15B, TMSB15B, MYO10, ANLN, TNNT1, ABLIM3, FMNL2, or LIMA1 (e.g., EVL); and b) recommending anti-estrogen therapy when said level of expression of the tumor marker is lower than a reference level and recommending not administering anti-estrogen therapy when the level of expression of the tumor marker is higher than the reference level.

The present disclosure is not limited to particular anti-estrogen therapies. Examples include, but are not limited to, an estrogen receptor antagonist or an aromatase inhibitor (e.g., tamoxifen, fulvestrant, toremifene, letrozole, anastrozole, or exemestane).

The present disclosure is not limited to particular samples. Examples include, but are not limited to tissue, blood, plasma, serum, or breast (e.g., breast cancer) cells. In some embodiments, the breast cells are estrogen receptor positive breast cancer cells.

The present disclosure is exemplified with breast cancer. However, in some embodiments, the described methods find use in treating additional cancers.

In some embodiments, estrogen promotes the generation of Suppressive Cortical Actin Bundles (SCABs).

In some embodiments, the method further comprises administering chemotherapy.

The present disclosure is not limited to particular reference levels of tumor markers such as EVL. In some embodiments, the reference level is the level of expression in estrogen receptor negative breast cancer cells.

Additional embodiments are described herein.

DEFINITIONS

Figure 1:
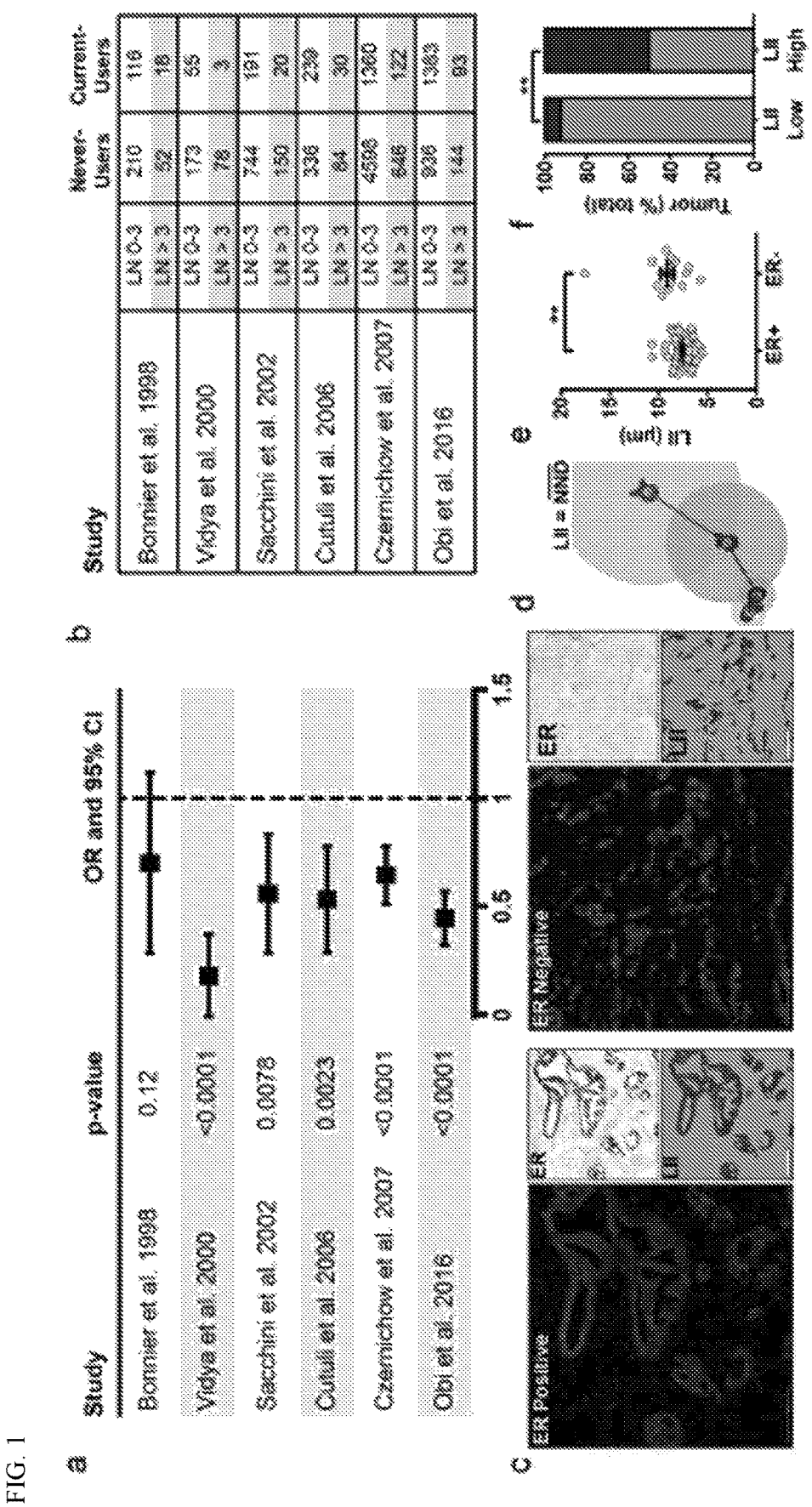
FIG. 1. ER expression is associated with low dissemination of breast cancer cells. Meta-Analysis of LN Dissemination: (a) Forest plot showing Odds Ratio, with 95% Confidence Interval (OR, 95% CI) of LN>3 in current-users compared with never-users of HRT. (b) Table reporting number of current-users and never-users with either LN≤3 or LN>3 in the studies analyzed in (a). Analysis of TMA #1 (CDP-BCP-TMA): (c) Representative images of ER+ (left panel) and ER-(right panel) tumors. (d) Illustration of Local Invasion Index (LII) measurement. (e) Scatter plot showing quantification of LII in ER+ and ER-tumors; mean+s.e.m. p=0.001. (f) Percentage bar graph showing ER status of tumors with Low (≤7 µm) and High (≥9 µm) LII. Analysis of TMA #2 (Cedars-Sinai LumB TMA): (g) Representative images of luminal-B breast tumors with high (top panel) or low (bottom panel) ER expression. In each panel, top-right inset shows ER staining and bottom-right inset shows binary masks of cytokeratin stain (black) and nuclei. Scale bar is 100 µm. (h) Scatter Plot of LII and ER levels. (i) ER levels in tumors with Low (≤7 µm) and High (≥9 µm) LII; mean+s.e.m. **p<0.0001. Quantification of Invasion In Vitro: (j) Illustration of 3D culture system. (k) Maximum intensity projections of confocal z-series of ER+ breast cancer MCF7 cells treated with drug vehicle, estradiol (E2) or fulvestrant (fulv). (1) Quantification of invasion.
Figure 1:
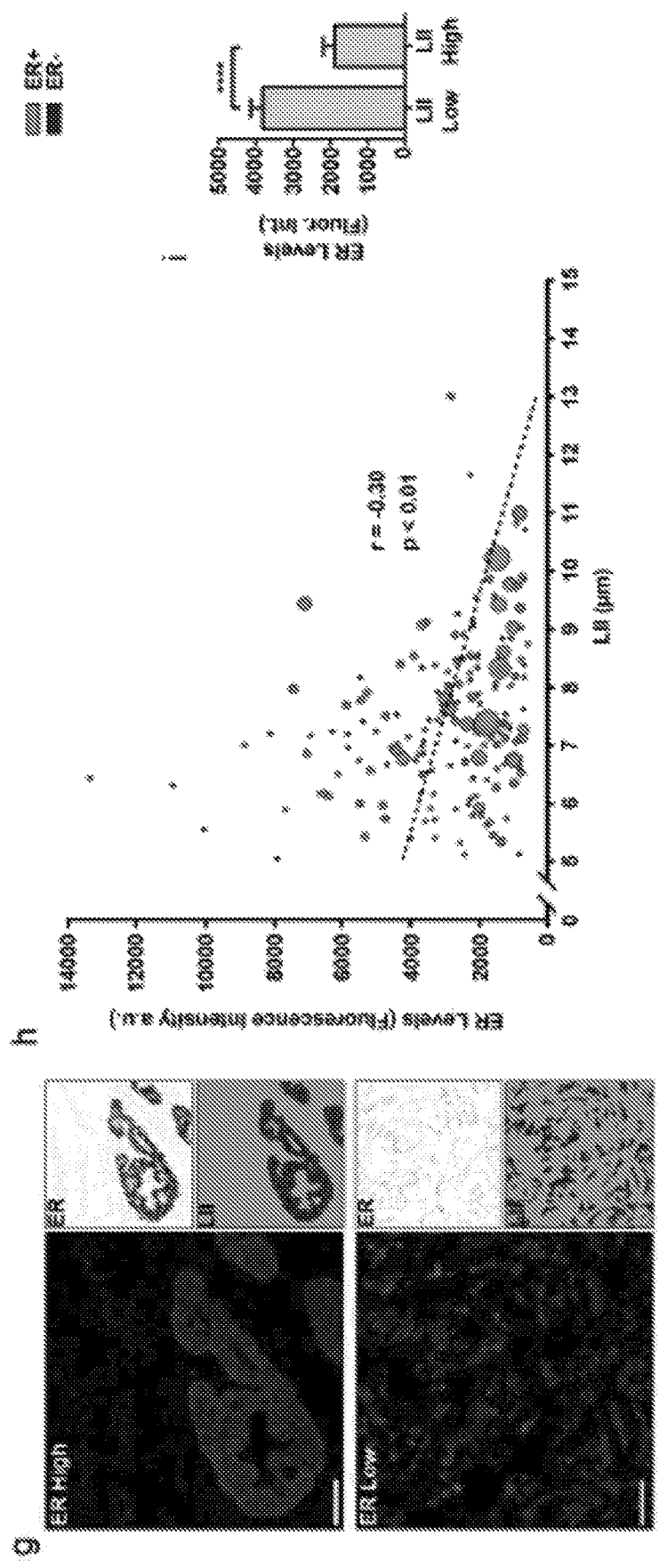
Figure 1:
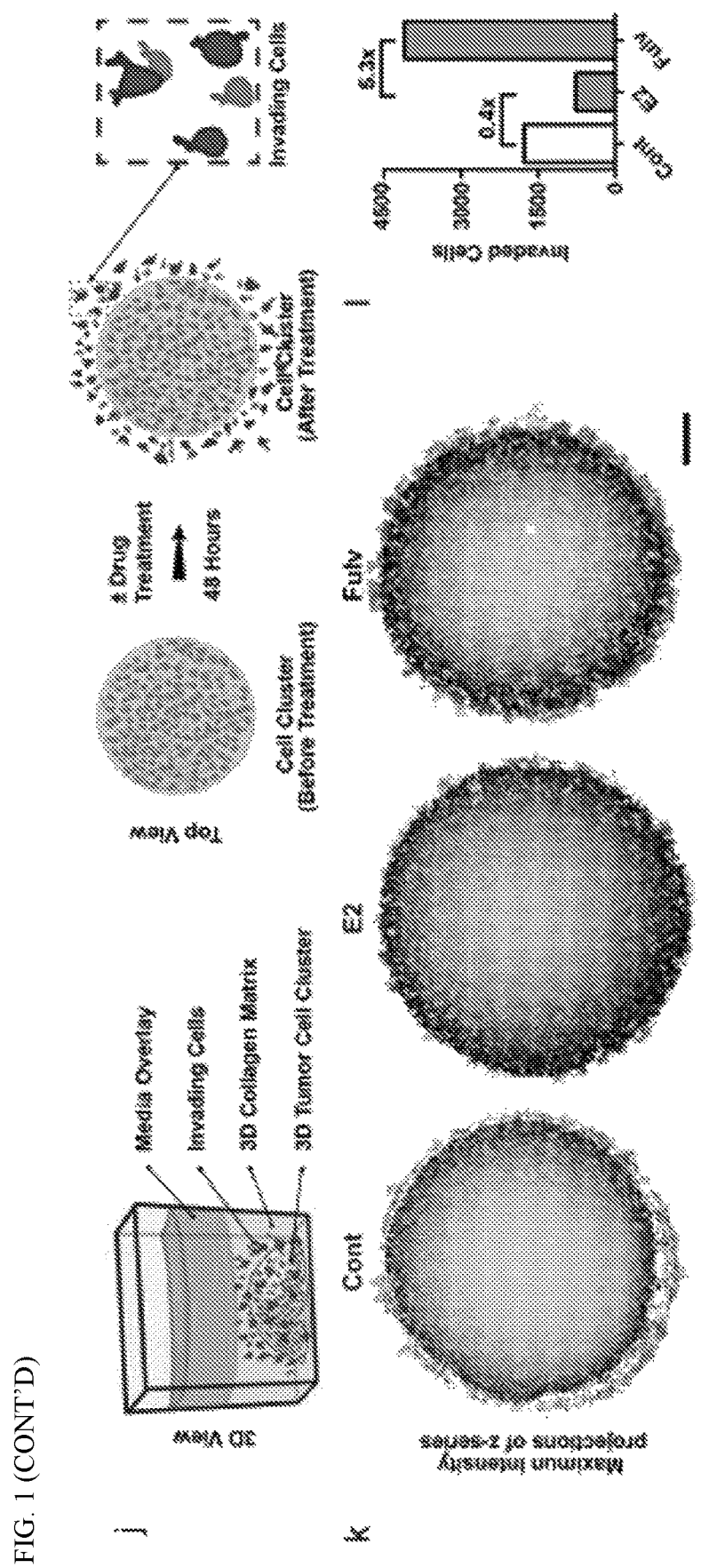

To facilitate an understanding of the present invention, a number of terms and phrases are defined below:

As used herein, the terms "detect", "detecting" or "detection" may describe either the general act of discovering or discerning or the specific observation of a detectably labeled composition.

As used herein, the term "subject" refers to any organisms that are screened using the diagnostic methods described herein. Such organisms preferably include, but are not limited to, mammals (e.g., humans).

The term "diagnosed," as used herein, refers to the recognition of a disease by its signs and symptoms, or genetic analysis, pathological analysis, histological analysis, and the like.

As used herein, the term "characterizing cancer in a subject" refers to the identification of one or more properties of a cancer sample in a subject, including but not limited to, the presence of benign, pre-cancerous or cancerous tissue, the stage of the cancer, and the subject's prognosis. Cancers may be characterized by the identification of the expression of one or more cancer marker genes, including but not limited to, EVL and/or ER.

As used herein, the term "stage of cancer" refers to a qualitative or quantitative assessment of the level of advancement of a cancer. Criteria used to determine the stage of a cancer include, but are not limited to, the size of the tumor and the extent of metastases (e.g., localized or distant).

As used herein, the term "nucleic acid molecule" refers to any nucleic acid containing molecule, including but not limited to, DNA or RNA. The term encompasses sequences that include any of the known base analogs of DNA and RNA including, but not limited to, 4-acetylcytosine, 8-hydroxy-N6-methyladenosine, aziridinylcytosine, pseudoisocytosine, 5-(carboxyhydroxylmethyl) uracil, 5-fluorouracil, 5-bromouracil, 5-carboxymethylaminomethyl-2-thiouracil, 5-carboxymethylaminomethyluracil, dihydrouracil, inosine, N6-isopentenyladenine, 1-methyladenine, 1-methylpseudouracil, 1-methylguanine, 1-methylinosine, 2,2-dimethylguanine, 2-methyladenine, 2-methylguanine, 3-methylcytosine, 5-methylcytosine, N6-methyladenine, 7-methylguanine, 5-methylaminomethyluracil, 5-methoxyaminomethyl-2-thiouracil, beta-D-mannosylqueosine, 5'-methoxycarbonylmethyluracil, 5-methoxyuracil, 2-methylthio-N6-isopentenyladenine, uracil-5-oxyacetic acid methylester, uracil-5-oxyacetic acid, oxybutoxosine, pseudouracil, queosine, 2-thiocytosine, 5-methyl-2-thiouracil, 2-thiouracil, 4-thiouracil, 5-methyluracil, N-uracil-5-oxyacetic acid methylester, uracil-5-oxyacetic acid, pseudouracil, queosine, 2-thiocytosine, and 2,6-diaminopurine.

The term "gene" refers to a nucleic acid (e.g., DNA) sequence that comprises coding sequences necessary for the production of a polypeptide, precursor, or RNA (e.g., rRNA, tRNA). The polypeptide can be encoded by a full length coding sequence or by any portion of the coding sequence so long as the desired activity or functional properties (e.g., enzymatic activity, ligand binding, signal transduction, immunogenicity, etc.) of the full-length or fragments are retained. The term also encompasses the coding region of a structural gene and the sequences located adjacent to the coding region on both the 5' and 3' ends for a distance of about 1 kb or more on either end such that the gene corresponds to the length of the full-length mRNA. Sequences located 5' of the coding region and present on the mRNA are referred to as 5' non-translated sequences. Sequences located 3' or downstream of the coding region and present on the mRNA are referred to as 3' non-translated sequences. The term "gene" encompasses both cDNA and genomic forms of a gene. A genomic form or clone of a gene contains the coding region interrupted with non-coding sequences termed "introns" or "intervening regions" or "intervening sequences." Introns are segments of a gene that are transcribed into nuclear RNA (hnRNA); introns may contain regulatory elements such as enhancers. Introns are removed or "spliced out" from the nuclear or primary transcript; introns therefore are absent in the messenger RNA (mRNA) transcript. The mRNA functions during translation to specify the sequence or order of amino acids in a nascent polypeptide.

As used herein, the term "oligonucleotide," refers to a short length of single-stranded polynucleotide chain. Oligonucleotides are typically less than 200 residues long (e.g., between 15 and 100), however, as used herein, the term is also intended to encompass longer polynucleotide chains. Oligonucleotides are often referred to by their length. For example a 24 residue oligonucleotide is referred to as a "24-mer". Oligonucleotides can form secondary and tertiary structures by self-hybridizing or by hybridizing to other polynucleotides. Such structures can include, but are not limited to, duplexes, hairpins, cruciforms, bends, and triplexes.

The term "isolated" when used in relation to a nucleic acid, as in "an isolated oligonucleotide" or "isolated polynucleotide" refers to a nucleic acid sequence that is identified and separated from at least one component or contaminant with which it is ordinarily associated in its natural source. Isolated nucleic acid is such present in a form or setting that is different from that in which it is found in nature. In contrast, non-isolated nucleic acids as nucleic acids such as DNA and RNA found in the state they exist in nature. For example, a given DNA sequence (e.g., a gene) is found on the host cell chromosome in proximity to neighboring genes; RNA sequences, such as a specific mRNA sequence encoding a specific protein, are found in the cell as a mixture with numerous other mRNAs that encode a multitude of proteins. However, isolated nucleic acid encoding a given protein includes, by way of example, such nucleic acid in cells ordinarily expressing the given protein where the nucleic acid is in a chromosomal location different from that of natural cells, or is otherwise flanked by a different nucleic acid sequence than that found in nature. The isolated nucleic acid, oligonucleotide, or polynucleotide may be present in single-stranded or double-stranded form. When an isolated nucleic acid, oligonucleotide or polynucleotide is to be utilized to express a protein, the oligonucleotide or polynucleotide will contain at a minimum the sense or coding strand (i.e., the oligonucleotide or polynucleotide may be single-stranded), but may contain both the sense and anti-sense strands (i.e., the oligonucleotide or polynucleotide may be double-stranded).

As used herein, the term "sample" is used in its broadest sense. In one sense, it is meant to include a specimen or culture obtained from any source, as well as biological and environmental samples. Biological samples may be obtained from animals (including humans) and encompass fluids, solids, tissues (e.g., biopsy samples), cells, and gases. Biological samples include blood products, such as plasma, serum and the like. Such examples are not however to be construed as limiting the sample types applicable to the present invention.

DETAILED DESCRIPTION OF THE INVENTION

Most ER+ breast cancer patients receive extended adjuvant anti-estrogenic therapies. Despite the overwhelming evidence demonstrating the efficacy of these therapies in reducing tumor recurrence, about one third of treated patients are afflicted with recurrent, highly invasive tumors (Sweeney et al., Hormone Molecular Biology and Clinical Investigation 9, 143-163 (2012)). Experiments described herein describe how ER inhibition may down-regulate EVL and aggravate tumor invasion and dissemination of these recurrent tumors. The experiments described herein advance understanding of the protective actions of estrogen against ER+ breast cancer progression via EVL, which promotes the generation of Suppressive Cortical Actin Bundles (SCABs) that inhibit motility dynamics, and provide a basis for customized therapy for such patients.

Accordingly, in some embodiments, the present disclosure provides compositions, systems, and methods for characterizing, recommending treatment, and provided treatment for cancer patients (e.g., ER+ breast cancer patients). For example, in some embodiments, levels of EVL or related genes (e.g., TMSB15B, TMSB15B, MYO10, ANLN, TNNT1, ABLIM3, FMNL2, or LIMA1) is used to characterizing, recommend a treatment, or provide a treatment for cancer patients (e.g., ER+ breast cancer patients).

In some embodiments, patients with tumors that exhibit low levels of EVL or related genes (e.g., relative to a reference level) and have tumors that express estrogen receptor are administered standard anti-estrogen therapies (an estrogen receptor antagonist or an aromatase inhibitor (e.g., tamoxifen, fulvestrant, toremifene, letrozole, anastrozole, or exemestane)). Without being limited to a mechanism, is it contemplated that such patients do not exhibit EVL mediated estrogen-sensitive formation of SCABs and are thus not subject to the protective effects of estrogen. It is contemplated that such patients benefit from standard anti-estrogen therapies.

In some embodiments, patients with tumors that exhibit high levels of EVL (e.g., relative to a reference level) or related genes are not administered anti-estrogen therapy (e.g., patients that have tumors that are positive or negative for estrogen receptor expression).

In some embodiments, patients with low levels of EVL are administered estrogen therapy (e.g. to promote EVL mediated generation of SCABs). In some embodiments, the estrogen therapy replaces anti-estrogen therapy.

It is further contemplated that the invasive potential of breast cancer is regulated by distinct actin cytoskeletal remodeling programs that are influenced by the tumor microenvironment (TME). More specifically, it is contemplated that the TME modulates ERa expression in both genomic and extranuclear pathways, and affects actin dynamics and cell motility. The actin cytoskeleton of the cancer cell constantly remodels, forming protrusions, blebs, focal adhesions and other invasive architectures that allow the cells to migrate in an invasive and directional response to microenvironmental cues.

ER positivity in breast cancer has been demonstrated to increase proliferation, however, in terms of migration may have a dichotomous role dependent on TME context. Data demonstrates that ERa suppresses migration in a chemotactic context but promotes migration in a durotactic context. As breast cancer progresses, they tend to become more fibrotic, creating a stiff microenvironment and shifting the way cells migrate and become invasive. This shift in the mode of migration provides a mechanism for the cells to evade therapies focused on targeting the more characterized and well-studied chemotactic migration. Accordingly, in some embodiments, the level of fibrosis of cancer samples is assayed to determine a treatment. For example, in some embodiments, subjects with high levels of fibrosis (e.g., subjects with high EVL) are administered anti-estrogen therapy (e.g., instead of estrogen therapy). It is contemplated that in these subjects, the administration of anti-estrogen therapy prevents estrogen-receptor mediated invasion.

In some embodiments, estrogen is give after or before anti-estrogen therapy. In some embodiments, estrogen is given to subjects that do not respond (e.g., do not exhibit a decrease in tumor size or spread or stasis of tumor size or spread) to anti-estrogen therapy.

The present disclosure is not limited to particular values for a reference level of EVL or related tumor markers. In some embodiments, the reference level is the level of EVL in ER− breast cancer cells. In some embodiments, the reference level is an average of a given population of cells or samples obtained from a representative number of patients. In some embodiments, the reference level is preset. In some embodiments, the reference level is based on the level of expression of EVL or related tumor marker genes in the patient (e.g., a non-cancer breast cell or other cell).

In some embodiments, patient administered estrogen or anti-estrogen are further administered additional chemotherapy agents (e.g. agents commonly used to treat breast cancer). The particular chemotherapy agent is based on a recommended treatment that considers the subject's age, stage of cancer, menopausal status, and presence of markers on the cancer cell. Examples include, but are not limited to, anthracyclines, such as doxorubicin, pegylated liposomal doxorubicin, and epirubicin, taxanes, such as paclitaxel, albumin-bound paclitaxel, and docetaxel, 5-fluorouracil (5-FU), cyclophosphamide, carboplatin, platinum agents (e.g., cisplatin, carboplatin), vinorelbine, capecitabine, gemcitabine, ixabepilone, eribulin, trastuzumab, pertuzumab, ado-trastuzumab emtansine, lapatinib, neratinib, palbociclib, ribociclib, abemaciclib, everolimus, and olaparib.

In some embodiments, patients currently undergoing cancer treatment (e.g., with anti-estrogen therapy or other chemotherapy) are screened for the presence or absence of altered levels of EVL. In some embodiments, treatment is modified based on the levels of EVL (e.g., adding or starting estrogen or anti-estrogen therapy).

In some embodiments, assays for levels of EVL are repeated (e.g., before, during or after anticancer treatment).

In some embodiments, assays are repeated daily, weekly, monthly, annually, or less often.

The present disclosure is not limited to particular methods of measuring the level of expression of EVL or related genes. Any patient sample may be tested according to methods of embodiments of the present invention. By way of non-limiting examples, the sample may be tissue (e.g., a breast biopsy sample), blood, or a fraction thereof (e.g., plasma, serum, cells), or circulating tumor cells.

In some embodiments, the level of expression of EVL is determined using a variety of nucleic acid techniques, including but not limited to: nucleic acid sequencing; nucleic acid hybridization; and, nucleic acid amplification.

A variety of nucleic acid sequencing methods are contemplated for use in the methods of the present disclosure including, for example, chain terminator (Sanger) sequencing, dye terminator sequencing, and high-throughput sequencing methods. Many of these sequencing methods are well known in the art. See, e.g., Sanger et al., Proc. Natl. Acad. Sci. USA 74:5463-5467 (1997); Maxam et al., Proc. Natl. Acad. Sci. USA 74:560-564 (1977); Drmanac, et al., Nat. Biotechnol. 16:54-58 (1998); Kato, Int. J. Clin. Exp. Med. 2:193-202 (2009); Ronaghi et al., Anal. Biochem. 242:84-89 (1996); Margulies et al., Nature 437:376-380 (2005); Ruparel et al., Proc. Natl. Acad. Sci. USA 102:5932-5937 (2005), and Harris et al., Science 320:106-109 (2008); Levene et al., Science 299:682-686 (2003); Korlach et al., Proc. Natl. Acad. Sci. USA 105:1176-1181 (2008); Branton et al., Nat. Biotechnol. 26(10):1146-53 (2008); Eid et al., Science 323:133-138 (2009); each of which is herein incorporated by reference in its entirety.

Next-generation sequencing (NGS) methods share the common feature of massively parallel, high-throughput strategies, with the goal of lower costs in comparison to older sequencing methods (see, e.g., Voelkerding et al., Clinical Chem., 55: 641-658, 2009; MacLean et al., Nature Rev. Microbiol., 7: 287-296; each herein incorporated by reference in their entirety). NGS methods can be broadly divided into those that typically use template amplification and those that do not. Amplification-requiring methods include pyrosequencing commercialized by Roche as the 454 technology platforms (e.g., GS 20 and GS FLX), the Solexa platform commercialized by Illumina, and the Supported Oligonucleotide Ligation and Detection (SOLiD) platform commercialized by Applied Biosystems. Non-amplification approaches, also known as single-molecule sequencing, are exemplified by the HeliScope platform commercialized by Helicos BioSciences, and emerging platforms commercialized by VisiGen, Oxford Nanopore Technologies Ltd., Life Technologies/Ion Torrent, and Pacific Biosciences, respectively.

Illustrative non-limiting examples of nucleic acid hybridization techniques include, but are not limited to, in situ hybridization (ISH), microarray, and Southern or Northern blot. In situ hybridization (ISH) is a type of hybridization that uses a labeled complementary DNA or RNA strand as a probe to localize a specific DNA or RNA sequence in a portion or section of tissue (in situ), or, if the tissue is small enough, the entire tissue (whole mount ISH). DNA ISH can be used to determine the structure of chromosomes. RNA ISH is used to measure and localize mRNAs and other transcripts within tissue sections or whole mounts. Sample cells and tissues are usually treated to fix the target transcripts in place and to increase access of the probe. The probe hybridizes to the target sequence at elevated temperature, and then the excess probe is washed away. The probe that was labeled with either radio-, fluorescent- or antigen-labeled bases is localized and quantitated in the tissue using either autoradiography, fluorescence microscopy or immunohistochemistry, respectively. ISH can also use two or more probes, labeled with radioactivity or the other non-radioactive labels, to simultaneously detect two or more transcripts.

In some embodiments, EVL levels are detected using fluorescence in situ hybridization (FISH). In some embodiments, FISH assays utilize bacterial artificial chromosomes (BACs). These have been used extensively in the human genome sequencing project (see Nature 409: 953-958 (2001)) and clones containing specific BACs are available through distributors that can be located through many sources, e.g., NCBI. Each BAC clone from the human genome has been given a reference name that unambiguously identifies it. These names can be used to find a corresponding GenBank sequence and to order copies of the clone from a distributor.

The present invention further provides a method of performing a FISH assay on human cells (e.g., breast or endometrial cells). Specific protocols are well known in the art and can be readily adapted for the present invention. Guidance regarding methodology may be obtained from many references including: *In situ Hybridization: Medical Applications* (eds. G. R. Coulton and J. de Belleroche), Kluwer Academic Publishers, Boston (1992); *In situ Hybridization: In Neurobiology; Advances in Methodology* (eds. J. H. Eberwine, K. L. Valentino, and J. D. Barchas), Oxford University Press Inc., England (1994); *In situ Hybridization: A Practical Approach* (ed. D. G. Wilkinson), Oxford University Press Inc., England (1992)); Kuo, et al., Am. J. Hum. Genet. 49:112-119 (1991); Klinger, et al., Am. J. Hum. Genet. 51:55-65 (1992); and Ward, et al., Am. J. Hum. Genet. 52:854-865 (1993)). There are also kits that are commercially available and that provide protocols for performing FISH assays (available from e.g., Oncor, Inc., Gaithersburg, MD). Patents providing guidance on methodology include U.S. Pat. Nos. 5,225,326; 5,545,524; 6,121,489 and 6,573,043. All of these references are hereby incorporated by reference in their entirety and may be used along with similar references in the art and with the information provided in the Examples section herein to establish procedural steps convenient for a particular laboratory.

Different kinds of biological assays are called microarrays including, but not limited to: DNA microarrays (e.g., cDNA microarrays and oligonucleotide microarrays); protein microarrays; tissue microarrays; transfection or cell microarrays; chemical compound microarrays; and, antibody microarrays. A DNA microarray, commonly known as gene chip, DNA chip, or biochip, is a collection of microscopic DNA spots attached to a solid surface (e.g., glass, plastic or silicon chip) forming an array for the purpose of expression profiling or monitoring expression levels for thousands of genes simultaneously. The affixed DNA segments are known as probes, thousands of which can be used in a single DNA microarray. Microarrays can be used to identify disease genes or transcripts (e.g., EVL) by comparing gene expression in disease and normal cells or other populations. Microarrays can be fabricated using a variety of technologies, including but not limiting: printing with fine-pointed pins onto glass slides; photolithography using pre-made masks; photolithography using dynamic micromirror devices; ink-jet printing; or, electrochemistry on microelectrode arrays.

Southern and Northern blotting is used to detect specific DNA or RNA sequences, respectively. DNA or RNA extracted from a sample is fragmented, electrophoretically separated on a matrix gel, and transferred to a membrane filter. The filter bound DNA or RNA is subject to hybridization with a labeled probe complementary to the sequence of interest. Hybridized probe bound to the filter is detected. A variant of the procedure is the reverse Northern blot, in which the substrate nucleic acid that is affixed to the membrane is a collection of isolated DNA fragments and the probe is RNA extracted from a tissue and labeled.

Nucleic acids may be amplified prior to or simultaneous with detection. Illustrative non-limiting examples of nucleic acid amplification techniques include, but are not limited to, polymerase chain reaction (PCR), reverse transcription polymerase chain reaction (RT-PCR), transcription-mediated amplification (TMA), ligase chain reaction (LCR), strand displacement amplification (SDA), and nucleic acid sequence based amplification (NASBA). Those of ordinary skill in the art will recognize that certain amplification techniques (e.g., PCR) require that RNA be reversed transcribed to DNA prior to amplification (e.g., RT-PCR), whereas other amplification techniques directly amplify RNA (e.g., TMA and NASBA).

In some embodiments, levels of EVL or related polypeptides are detected (e.g., using immunoassays or mass spectrometry).

Illustrative non-limiting examples of immunoassays include, but are not limited to: immunoprecipitation; Western blot; ELISA; immunohistochemistry; immunocytochemistry; flow cytometry; and, immuno-PCR. Polyclonal or monoclonal antibodies detectably labeled using various techniques known to those of ordinary skill in the art (e.g., colorimetric, fluorescent, chemiluminescent or radioactive) are suitable for use in the immunoassays. Immunoprecipitation is the technique of precipitating an antigen out of solution using an antibody specific to that antigen. The process can be used to identify protein complexes present in cell extracts by targeting a protein believed to be in the complex. The complexes are brought out of solution by insoluble antibody-binding proteins isolated initially from bacteria, such as Protein A and Protein G. The antibodies can also be coupled to sepharose beads that can easily be isolated out of solution. After washing, the precipitate can be analyzed using mass spectrometry, Western blotting, or any number of other methods for identifying constituents in the complex.

A Western blot, or immunoblot, is a method to detect protein in a given sample of tissue homogenate or extract. It uses gel electrophoresis to separate denatured proteins by mass. The proteins are then transferred out of the gel and onto a membrane, typically polyvinyldiflroride or nitrocellulose, where they are probed using antibodies specific to the protein of interest. As a result, researchers can examine the amount of protein in a given sample and compare levels between several groups.

An ELISA, short for Enzyme-Linked ImmunoSorbent Assay, is a biochemical technique to detect the presence of an antibody or an antigen in a sample. It utilizes a minimum of two antibodies, one of which is specific to the antigen and the other of which is coupled to an enzyme. The second antibody will cause a chromogenic or fluorogenic substrate to produce a signal. Variations of ELISA include sandwich ELISA, competitive ELISA, and ELISPOT. Because the ELISA can be performed to evaluate either the presence of antigen or the presence of antibody in a sample, it is a useful tool both for determining serum antibody concentrations and also for detecting the presence of antigen.

Immuno-polymerase chain reaction (IPCR) utilizes nucleic acid amplification techniques to increase signal generation in antibody-based immunoassays. Because no protein equivalence of PCR exists, that is, proteins cannot be replicated in the same manner that nucleic acid is replicated during PCR, the only way to increase detection sensitivity is by signal amplification. The target proteins are bound to antibodies which are directly or indirectly conjugated to oligonucleotides. Unbound antibodies are washed away and the remaining bound antibodies have their oligonucleotides amplified. Protein detection occurs via detection of amplified oligonucleotides using standard nucleic acid detection methods, including real-time methods.

Mass spectrometry has proven to be a valuable tool for the determination of molecular structures of molecules of many kinds, including biomolecules, and is widely practiced today. Purified proteins are digested with specific proteases (e.g. trypsin) and evaluated using mass spectrometry. Many alternative methods can also be used. For instance, either matrix-assisted laser desorption/ionization (MALDI) or electrospray ionization (ESI) mass spectrometric methods can be used. Furthermore, mass spectroscopy can be coupled with the use of two-dimensional gel electrophoretic separation of cellular proteins as an alternative to comprehensive pre-purification. Mass spectrometry can also be coupled with the use of peptide fingerprint database and various searching algorithms. Differences in post-translational modification, such as phosphorylation or glycosylation, can also be probed by coupling mass spectrometry with the use of various pretreatments such as with glycosylases and phosphatases. All of these methods are to be considered as part of this application.

In some embodiments, electrospray ionisation quadrupole mass spectrometry is utilized to detect EVL levels (See e.g., U.S. Pat. No. 8,658,396; herein incorporated by reference in its entirety).

The present disclosure is not limited to particular methods of measuring fibrosis. In some embodiments, the level of fibrosis is measured using matrix-specific staining protocols (e.g., using haematoxylin and eosin stain or other stains). In some embodiments, the level of fibrosis is quantitated.

In some embodiments, a computer-based analysis program is used to translate the raw data generated by the detection assay (e.g., the presence, absence, or amount of a given marker or markers) into data of predictive value for a clinician. The clinician can access the predictive data using any suitable means. Thus, in some preferred embodiments, the present invention provides the further benefit that the clinician, who is not likely to be trained in genetics or molecular biology, need not understand the raw data. The data is presented directly to the clinician in its most useful form. The clinician is then able to immediately utilize the information in order to optimize the care of the subject.

The present invention contemplates any method capable of receiving, processing, and transmitting the information to and from laboratories conducting the assays, information provides, medical personal, and subjects. For example, in some embodiments of the present invention, a sample (e.g., a biopsy or a serum sample) is obtained from a subject and submitted to a profiling service (e.g., clinical lab at a medical facility, genomic profiling business, etc.), located in any part of the world (e.g., in a country different than the country where the subject resides or where the information is ultimately used) to generate raw data. Where the sample comprises a tissue or other biological sample, the subject may visit a medical center to have the sample obtained and sent to the profiling center, or subjects may collect the sample themselves and directly send it to a profiling center. Where the sample comprises previously determined biological information, the information may be directly sent to the profiling service by the subject (e.g., an information card containing the information may be scanned by a computer and the data transmitted to a computer of the profiling center using an electronic communication systems). Once received by the profiling service, the sample is processed and a profile is produced (i.e., EVL or other marker expression levels), specific for the information desired for the subject.

The profile data is then prepared in a format suitable for interpretation by a treating clinician. For example, rather than providing raw expression data, the prepared format may represent a assay result (e.g., EVL level) for the subject, along with recommendations for particular treatment options. The data may be displayed to the clinician by any suitable method. For example, in some embodiments, the profiling service generates a report that can be printed for the clinician (e.g., at the point of care) or displayed to the clinician on a computer monitor.

In some embodiments, the information is first analyzed at the point of care or at a regional facility. The raw data is then sent to a central processing facility for further analysis and/or to convert the raw data to information useful for a clinician or patient. The central processing facility provides the advantage of privacy (all data is stored in a central facility with uniform security protocols), speed, and uniformity of data analysis. The central processing facility can then control the fate of the data following treatment of the subject. For example, using an electronic communication system, the central facility can provide data to the clinician, the subject, or researchers.

In some embodiments, the subject is able to directly access the data using the electronic communication system. The subject may chose further intervention or counseling based on the results. In some embodiments, the data is used for research use. For example, the data may be used to further optimize the inclusion or elimination of markers as useful indicators of a particular condition or stage of disease or as a companion diagnostic to determine a treatment course of action.

Compositions for use in the screening, diagnostic, prognostic, and therapeutic methods described herein include, but are not limited to, probes, amplification oligonucleotides, and the like. In some embodiments, compositions are provided in the form of a kit. In some embodiments, kits include all components necessary, sufficient or useful for detecting the markers described herein (e.g., reagents, controls, instructions, etc.). The kits described herein find use in research, therapeutic, screening, and clinical applications.

The probe and antibody compositions of the present invention may also be provided in the form of an array.

In some embodiments, the present invention provides one or more nucleic acid probes or primers having 8 or more (e.g., 10 or more, 12 or more, 15 or more, 18 or more, etc.) nucleotides, and that specifically bind to nucleic acids encoding EVL.

Embodiments of the present invention provide complexes of EVL nucleic acids or polypeptides with nucleic acid primers or probes or antibodies. In some embodiments, a reaction mixture comprising an EVL polypeptide and an antibody that specifically binds to EVL is provided. In some embodiments, the present invention provides a multiplex (e.g., microarray) comprising reagents that binds to EVL and one or more additional amino acid or nucleic acids.

EXPERIMENTAL

The following examples are provided in order to demonstrate and further illustrate certain preferred embodiments and aspects of the present invention and are not to be construed as limiting the scope thereof.

Example 1

Methods

Materials and Methods

Antibodies and Reagents.

The following antibodies were used: Human anti-phospho-(Thr18/Ser19) Myosin Light Chain 2 no. 3674 (Cell Signaling), Human anti-Arp2/3 clone no.13C9 (Millipore), Human anti-pan cytokeratin no. AE1/AE3 (DAKO), Human anti-ER no. H4624 (Invitrogen), Human anti-EVL no. HPA018849 (Sigma Prestige), Human anti-EVL (a gift from Frank Gertler), Human anti-Actin (abcam—ab3280). The following reagents were used: ALEXA FLUOR 568-Phalloidin dye (Thermo-Fisher), ALEXA FLUOR 647-Phalloidin dye; (Thermo-Fisher), Hoechst 33342 (Thermo-Scientific), β-estradiol (Sigma-Aldrich), Tamoxifen (Sigma-Aldrich), Fulvestrant (Sigma-Aldrich), ROCK inhibitor (γ-27632; Tocris), Insulin growth factor 1 human recombinant (Sigma-Aldrich), Puromycin (Thermo-Scientific), G418 (Life Technologies), POLYBRENE transfection reagent (EMD Millipore), Fugene HD (Life Technologies).

Analysis of Lymph Node (LN) Dissemination.

Lymph node (LN) dissemination was determined in a meta-analysis of epidemiological studies (Czernichow, C. Bulletin du Cancer 90, 821-831 (2007); Jones et al., The effect of hormone replacement therapy on prognostic indices in women with breast cancer. The Medical Journal of Australia (1994); Bonnier, P. et al. International Journal of Cancer 79, 278-282 (1998); Vidya, R. BMJ 321, 179-179 (2000); Delgado, R. C. & Lubian Lopez, D. M. Maturitas 38, 147-156 (2001); Sacchini, V. et al. Ann. Surg. Oncol. 9, 266-271 (2002); Cutuli, B. et al. Breast Cancer Res Treat 95, 55-64 (2006); Schuetz, F. et al. American Journal of Obstetrics and Gynecology 196, 342.e1-342.e9 (2007); Rauh, C. et al. Geburtshilfe Frauenheilkd 75, 588-596 (2015); Obi, N. et al. International Journal of Cancer 138, 2098-2108 (2016)). that investigated the effects of HRT on the clinical and prognostic characteristics of tumors in cohorts of breast cancer patients. Specifically, only studies that reported LN status in HRT current-users and never-users, with a minimum of 10 patients per treatment group, were included. Studies that investigated the effect of HRT on breast cancer incidence in healthy women, were not considered. This focused approach enriched for breast cancer patients on HRT, providing sufficient data for a robust quantification of LN dissemination under estrogen treatment. For patient inclusion criteria, the analysis included only postmenopausal breast cancer patients (older than 50 years of age and had at least 6 months of amenorrhea or had double oophorectomy), who were on HRT for at least 6 months before diagnosis (denoted as current-users) or who never used HRT (denoted as never-users); HRT included treatment with estrogen alone or estrogen plus progestin. Patients taking estriol, a partial ER agonist available as a dietary supplement, were excluded from the analysis. This meta-analysis consisted of two parts: calculating Odds Ratio (OR) for having more than three positive LN (LN>3), using six studies (Czernichow, supra; Bonnier et al., supra; Vidya, supra; Sacchini et al., supra; Cutuli et al., supra; Obi et al., supra); and calculating OR for having any number of positive LN (LN+), using nine studies (Jones et al., supra; Bonnier et al., supra; Delgado et al., supra; Vidya, supra;

Sacchini et al., supra; Cutuli et al., supra; Schuetz et al. supra; Rauh et al., supra; Obi et al., supra). For both analyses, Fisher's Exact Test was conducted to determine significance of each study. The odds ratio was determined for each study and the exact 95% confidence interval was calculated using SATA 14.0.

Local Invasion Index (LII) Analysis. Breast Cancer Tissue Microarrays (TMA).

Two independent breast cancer tissue microarray sets were used in this analysis: (TMA #1) Cancer Diagnostics Program (CDP) Breast Cancer Progression (BCP) TMA from the National Cancer Institute (NCI), comprised of an array of ER+ and ER− tumors; and (TMA #2) luminal B breast cancer TMA from Cedars-Sinai Medical Center comprised of an array of luminal B breast cancer tumors with varied levels of ER expression. LN status was indicated in the corresponding pathology report for each patient. Samples that were damaged or that exhibited high degree of inflammatory cell infiltration were excluded from the analysis. Local invasion Index (LII) Measurement. Cancer cell invasion was quantified in both TMAs (64 samples from the NCI CDP-BCP-TMA and 180 samples from the Cedars-Sinai lumB-TMA) by employing the nearest neighbor distance (NND) approach. Cancer cells were identified using a binary mask generated by thresholding the fluorescence signal of the cytokeratin stain. Using a built-in module in Nikon Elements, the distance between the nucleus of each cancer cell and the nucleus of the cell nearest to it was measured. Cells scattered at the periphery of the analyzed region were excluded from the analysis if their NND zone (circular zone with centroid as center and NND as radius) is not fully contained within the analyzed area. LII was calculated as the average NND of all cancer cells within the analyzed tumor area.

Three-Dimensional Culture System.

A tissue culture model system was designed to quantitate 3D invasion of cells with low invasive capacity; the configuration of this system allowed reliable monitoring of invading cells over a relatively long period of time (≥2 days). The system was setup in 8-well glass-bottom chamber slides (Labtek), where cancer cells were embedded in a central 3D matrix and allowed to invade into an encapsulating outer 3D matrix. Prior to utilization, the bottom coverslips of the chamber slides were silanized using 2% Aminopropyltrimethoxysilane (Acros Organics) in isopropanol for 10 min at room temperature, followed by repeated water washes and drying at 37° C. Chamber slides were then treated with 1% glutaraldehyde for 20 min at room temperature, followed by water washes and drying at 37° C., and finally sterilization under UV light for 15 min. After corresponding pretreatments, $1 \times 10^5$ cells/well were resuspended in 10 μL of 1 mg/mL type-I collagen containing 1.25 mg/mL polyethylene glycol diglycidyl ether (PEG-DE) (Fisher). Cell suspension was added at the center of the chamber wells and allowed to polymerize in the tissue culture incubator. The outer matrix, prepared similarly to the collagen mixture described above with the addition of 20 nM human recombinant IGF1, was added to encapsulate the central matrix; after polymerization, the setup was overlaid with growth media containing the corresponding treatments. Cells were allowed to invade into the outer matrix for 48 hours (with one media change at 24 hours), and then they were fixed and stained with Hoechst 33342 (Thermo Scientific) for 24 hours at 4° C. Confocal z-series of Hoechst and DIC were acquired at 1.5 μm z-steps on a Nikon Ti-E inverted microscope equipped with a 20× Plan Apo 0.75 NA Nikon objective, Photometrics CoolSNAP MYO CCD camera, motorized stage and a Crest XLIGHT spinning-disk confocal system. At each z-step, large-image stitching was used to generate a composite image of the entire area including the central matrix and the invaded cells. A binary mask was generated from the maximum intensity projection image of the z-series. A region of interest (ROI) was created by excluding the central area (determined using the overlaid DIC image) and the number of invading cells in the ROI was quantitated using the Object Count Nikon Elements module.

Kymography Analysis. Differential Interference Contrast (DIC) Microscopy Time-Lapse Imaging.

Cells were plated at 30% confluence on glass-bottom 6-well plate (MatTek) and allowed to adhere for 24 hours before experimentation. Cells were treated with E2 (10 nM), tam (1 μM), or fulv (100 nM) in complete growth media, which were replaced every 24 hours. Cells were imaged 72 hours after plating at 1 frame/sec for 45 min using differential interference contrast (DIC) microscopy. Images were acquired with a 60× Plan Apo 1.40 NA Nikon objective on a Nikon Ti-E inverted microscope equipped with a Hamamatsu ORCA-Flash 4.0 V2 cMOS camera, environmental chamber, motorized stage and maintained in focus using Nikon Perfect Focus System. Kymography Analysis of Membrane Ruffles. A kymograph was registered along the axis of ruffling at the site of highest membrane dynamics (as determined by minimum intensity projections). On the generated kymograph, membrane ruffles were identified as areas of high contrast. For each kymograph, two parameters of membrane ruffles were analyzed: frequency and speed. Frequency was determined by quantitating ruffle number (areas of high contrast) in each kymograph. Speed was determined as the distance traveled by a ruffle/time.

Volumetric Analysis. Cells were fixed with 4% PFA (Electron Microscopy Sciences) for 10 min at 37° C. PFA was quenched with 0.1M glycine and cells were permeabilized with 0.1% Triton X-100, both for 10 min at room temperature. The actin cytoskeleton was stained with ALEXA FLUOR conjugated phalloidin (ALEXA FLUOR 568- or ALEXA FLUOR 647-Phalloidin; Thermo-Fisher) diluted in PBS; nuclei were stain with Hoechst 33342 (Thermo Scientific). Slides were blocked in 1% FBS/1% BSA in PBS at room temperature for 1 hour. Cells were stained for phospho-MLC and Arp2/3, with primary and secondary antibodies diluted in blocking buffer and incubated using standard protocols. Confocal z-series were acquired at 0.2 μm z-steps on a Nikon Ti-E inverted microscope equipped with a 100× Plan Apo TIRF 1.49 NA Nikon objective, Photometrics COOLSNAP MYO CCD camera, motorized stage, a Crest XLIGHT Spinning Disk confocal system and a Lumencor SPECTRA X light source. Mean fluorescence intensity of phospho-MLC and Arp2/3 at the leading edge, was determined within a 3D volumetric binary mask, generated using the fluorescent signal of the actin stain. Nikon Elements 3D Object Module was used to construct the 3D binary mask from a series of 2D masks generated at each z-step in the actin channel. Importantly, to limit the analysis to the leading-edge actin, the masks were generated within an ROI that was restricted to a 3 μm wide band juxtaposed to the membrane.

Differential Gene Expression Analysis of Actin Cytoskeletal Regulators.

Gene Ontology (GO) Consortium search engine was used, with the search term "cytoskeleton", to generate a list of genes associated with the cytoskeleton. The initial list of 1000+ genes retuned in the GO search (www.geneotology.org) was further refined by selecting only cytoskeletal regulators that directly interact with actin, as determined by hand for each gene from an extensive literature review; this process generated a shorter list of 285 actin cytoskeletal regulators. Using public datasets available on ONCOMINE (www.oncomine.org) database, differential expression in ER+ breast cancer of the genes in the curated gene-set was analyzed. The following criteria for inclusion of studies were applied: 1) studies must have included clinical samples from patients (studies with only cell line data were excluded); 2) studies must have included both ER+ and ER-tumors, with a minimum of ten samples per group; and 3) microarray chips used in the studies must have had probes representing a minimum of 95% of the genes on the curated gene-set. Based on these criteria, 12 out of the 56 studies available on ONCOMINE database were selected. Data were presented in volcano plots to visualize both fold-change and significance, concomitantly. The thresholds for identifying a gene as a positive 'hit' were 2-fold change in expression (in either positive or negative direction) and $p \leq 0.05$.

Analysis of DCIS Index. Quantification of DCIS Index.

Large composite images of the entire mid-sections from each tumor sample were acquired using a 4× Plan Fluor 0.13 NA Nikon objective on a TI-Eclipse TE2000-U inverted microscope equipped with a Nikon DS-Fi2 color camera and motorized Prior stage. DCIS structures were identified as intact non-disseminated tumor structures and were counted in the composite images. In addition, tumor area, which encompasses the whole tumor region, and cellular area, which consists of only the area with cancer cells (excluding the stroma), were measured; the cellular coefficient was calculated as cellular area/tumor area. The DCIS index was calculated as the product of the number of DCIS structures multiplied by the cellular coefficient (to correct for differences in cellularity among tumors). The DCIS index was then normalized over the tumor area (to correct for differences in tumor size).

Interferometric Photoactivated Localization Microscopy (iPALM).

MCF7 cells, transduced with pCMV-mEos2-EVL-IRES-BlastR lentivirus, were cultured for 24 hours on 25 mm diameter coverslips containing gold nanoparticles (Nanopartz) that serve as iPALM calibration standards and drift correction fiducial markers (Shtengel, G. et al. Proc. Natl. Acad. Sci. U.S.A. 106, 3125-3130 (2009); Kanchanawong, P. et al. Nature 468, 580-584 (2010)). Cells were fixed using 2% PFA in PEM buffer (80 mM PIPES, 5 mM EGTA, 2 mM $MgCl_2$, pH6.8) and the actin cytoskeleton was stained using phalloidin conjugated to ALEXA FLUOR 647 (ThermoFisher Scientific) at a concentration of 2.5% (5units/mL). Immediately following labeling, samples were mounted in STORM buffer (100 mM MEA, 0.4 mg/mL glucose oxidase, and 24ug/mL catalase from Sigma), 10% glucose, 10 mM NaCl and 50 mM Tris-HCl pH 8.0. A second 18 mm diameter coverslip was adhered to the top of the sample and sealed to create an air-tight imaging volume, permitting sequential 3D super-resolution imaging of ALEXA FLUOR 647-Phalloidin via STORM and mEos2-EVL via PALM. Samples were imaged using interferometric photoactivation and localization microscopy, as previously described. Briefly, images were acquired via two 60x 1.49 NA TIRF objectives (Nikon), with signals from both combined in a custom three-way beamsplitter (Rocky Mountain Instruments), and imaged in 3 phase channels on EMCCD cameras (iXon DU-897, Andor Technology). ALEXA FLUOR 647-conjugated phalloidin dye was imaged first, using 642 nm laser excitation (OptoEngine LLC) operating at ca. 5 kW/cm2 at the sample, with camera exposure of 40 ms to acquire 60,000 raw frames. mEos2-EVL was imaged using 561 nm laser excitation (OptoEngine LLC) at ca. 2.5 kW/cm2, with 2-10 W/cm2 405 nm illumination (Coherent) for photoconversion of mEos2, and 50 ms camera exposure to acquire 50,000 raw images. Raw images were then subjected to iPALM localization, final image reconstruction, multichannel alignment and analysis using PeakSelector software (Sage, D. et al. Quantitative evaluation of software packages for single-molecule localization microscopy. Nat. Methods 12, 717-724 (2015)). Final en face and orthogonal ROIs are displayed as cumulative intensity projections of rendered localizations.

Statistical Analysis.

Unless indicated otherwise, statistical summaries are represented as mean+s.e.m or mean+s.d and statistical significance was determined using a two-tailed two sample t-test with Welsh correction. The nonparametric Mann-Whitney test was used in the presence of skewed data. The Pearson Correlation Coefficient was estimated to assess the relationship between continuous variables. For ChIP/qPCR experiments, p-values were generated by two-way ANOVA using the Sidak test for multiple comparison to one control. Survival was estimated using Kaplan-Meier plots. Comparison between survival curves was performed using the log-rank test.

Cell Culture.

MCF7 and HEK293T cells were cultured in high glucose DMEM base media with sodium pyruvate and L-glutamine (Corning) supplemented with additional 100 mM L-glutamine, 10% Fetal Bovine Serum (FBS; Gibco), and antibiotics (100 units/mL penicillin+100 m/mL streptomycin from Life Technologies, Inc.). T47D were cultured in RPMI1640 base media with L-glutamine (Corning) supplemented with additional 100 mM L-glutamine, 5 µg/mL insulin (Roche), 10% FBS and antibiotics. MCF10A were cultured in DMEM/F12 50/50 with L-glutamine (Corning), 5% Horse Serum, 20 ng/mL epidermal growth factor (EGF, Peprotech), 0.5 mg/mL hydrocortisone (Sigma), 100 ng/mL cholera toxin (Sigma), 10 µg/mL insulin and antibiotics. Caco2 were cultured in MEM base media with L-glutamine (Corning), 20% FBS, and antibiotics. MDCK were cultured in high glucose DMEM base media with sodium pyruvate and L-glutamine (Corning), 10% FBS, and antibiotics.

Plasmids.

The following plasmids were used for RNAi: pLKO.1-TRC cloning vector was a gift from David Root (Addgene plasmid #10878), pLKO EVL shRNA (GE Dharmacon TRCN0000063869, antisense TACTAGGATCTTCCATTTGGC (SEQ ID NO: 1)), TRIPZ (GE Dharmacon RHS4750), and TRIPZ EVL shRNA (GE Dharmacon PN V3THS_300209, antisense TGGCTTTCATCTTCCTTCT (SEQ ID NO: 2)), previously validated (Mouneimne, G. et al. Differential remodeling of actin cytoskeleton architecture by profilin isoforms leads to distinct effects on cell migration and invasion. Cancer Cell 22, 615-630 (2012)). MSCV-eGFP-EVL was a gift from Frank Gertler, MIT, used for retroviral expression in kymography experiments. Lentiviral construct pLenti CMV-MRLC1-mRuby2-IRES-PuroR was generated by PCR amplification of cDNA for *Homo sapiens* MRLC1 from eGFP-MRLC (a gift from Tom Egelhoff, Addgene #35680) and mRuby2-N1 (a gift from Michael Davidson, Addgene #54614) to create C-terminal tagged MRLC. Fusion construct was subcloned into the expression vector pCIG3 (pCMVIRES-GFP, a gift from Felicia Goodrum, Addgene plasmid #78264), modified to replace the GFP cassette with puromycin resistance gene. pCMV-iRFP670-EVL-IRES-BlastR was generated by PCR amplification of cDNA for *Mus musculus* EVL cDNA from MSCV-eGFP-EVL and piRFP670-N1 (a gift from Vladislav Verkhusha, Addgene #45457) to create N-terminal tagged EVL. Fusion construct was subcloned into pCIG3 modified to replace GFP with blasticidin resistance. Lentiviral expression constructs pLenti EF1a-eGFP-EVL, pLenti EF1a-eGFP, pLenti Lifeact-iRFP670-BlastR, and pLenti Lifeact-eGFP-BlastR were generated by Gateway technology (Thermo). pLenti EF1a-eGFP-EVL and pLenti EF1a-eGFP were generated by subcloning *Mus musculus* EVL cDNA from MSCV-eGFP-EVL into eGFP-C2 (Clontech). eGFP and eGFP-EVL were subcloned into Gateway entry vector pMuLE ENTR MCS L5-L2 (a gift from Ian Frew, Addgene plasmid #62085) modified to contain the hEF1a promoter, and recombined with pMuLE ENTR MCS L1-R5 (a gift from Ian Frew, Addgene plasmid #62084) and pLenti Dest PuroR R1-R2 using LR Clonase II (Thermo) to generate the final lentiviral expression vector. pLenti Lifeact-eGFP-BlastR and pLenti Lifeact-iRFP670-BlastR were generated by subcloning Lifeact-mEGFP (a gift from Michael Davidson, Addgene #54610), or Lifeact-iRFP670 into pMuLE ENTR MCS L1-R5, and recombined with pMuLE ENTR MCS L5-L2 and pLenti Dest BlastR. The following plasmids have been deposited to Addgene: pLenti CMV-MRLC1-mRuby2-IRES-PuroR (#103031), Lifeact-iRFP670 (#103032), pLenti Lifeact-iRFP670-BlastR (#84385), pLenti Lifeact-eGFP-BlastR (#84383), pENTR CMVie-Lifeact-iRFP670 L1-R5 (#84390), pENTR CMVie-Lifeact-EGFP L1-R5 (#84391), pLenti Dest BlastR R1-R2 (#84574), pLenti Dest PuroR R1-R2 (#84575).

Virus Production.

HEK293T cells were transfected at 60% confluence using Fugene HD (Promega) in OptiMEM (Corning) with transfer plasmid and second-generation lentiviral packaging system (psPAX2 and pMD2.G, Addgene #12260 and #12259, gifts from Didier Trono) or pCL-Ampho (Novus) for lentiviral or retroviral production, respectively. Virus was collected 48-72 hours post-transfection, clarified by 0.45-μm filters. Recipient cells were infected at 50% confluence with virus at a 1:1 dilution with their culturing media containing POLYBRENE transfection reagent (10ug/mL). Puromycin selection was started 36 hours post-infection.

Tissue Immunolabeling.

Slides were baked for 1 hour at 60° C., deparaffinized in xylene, and rehydrated in increasingly diluted ethanol solutions. Heat-Induced Epitope Retrieval (HIER) was performed (40 min boiling+20 min cooling) in Tris-EDTA pH9 buffer for anti-ER (Invitrogen, 1:50 dilution) and anti-EVL (Sigma Prestige, 1:50 dilution) antibodies and sodium citrate pH6 buffer for antipan cytokeratin AE1/AE3 (DAKO, 1:100 dilution). Following standard immunofluorescence staining protocol, samples were mounted in ProLong Diamond Antifade (Thermo-Fisher) and allowed to cure for at least 24 hours before imaging. Imaging. Tumors were imaged using a 20× Plan Apo 0.75 NA Nikon objective on a Nikon Ti-E inverted microscope equipped with a Hamamatsu ORCA-Flash 4.0 V2 cMOS camera, motorized stage and maintained in focus using Nikon Perfect Focus System. Large composite images of whole tumor sections were generated by digital stitching using Nikon Elements. Tumor sections that were damaged or that exhibited high degree of inflammatory cell infiltration were excluded from the analysis.

Proliferation Assay.

Cells were plated in a 6-well plate (25,000 cells per well) in growth media and allowed to adhere for 24 hours. A full media change with drug was performed every day and maintained for 48 hours, after which cells were trypsonized and quantified using a hemocytometer.

Immunofluorescence Staining.

Cells were fixed with 4% PFA (Electron Microscopy Sciences) for 10 min at 37° C. PFA was quenched with 0.1M glycine and cells were permeabilized with 0.1% Triton X-100, both for 10 min at room temperature. The actin cytoskeleton was stained with ALEXA FLUOR conjugated phalloidin dye (Alexa Fluor 568- or Alexa Fluor 647-Phalloidin; Thermo-Fisher) diluted to 2.5% in PBS; nuclei were stain with Hoechst 33342 (Thermo-Scientific); Phosphorylated myosin light chain was immunolabeled using human anti-phospho-(Thr18/Ser19) Myosin Light Chain 2 no. 3674 (Cell Signaling) at 1:100 dilution; Arp2/3 was immunolabeled using human anti-Arp2/3 clone no. 13C9 (Millipore) at 1:200 dilution; EVL was immunolabeled using human anti-EVL (a gift from Frank Gertler) at 1:50 dilution. Slides were blocked in 1% FBS/1% BSA in PBS; primary and secondary antibodies were diluted in blocking buffer and incubated using standard protocols. Samples were mounted in ProLong Diamond Antifade (Thermo-Fisher) and allowed to cure for at least 24 hours before imaging.

Quantification of EVL Protein by Immunofluorescence.

Cells were fixed and stained as described above and imaged using a 20× Plan Apo 0.75 NA Nikon objective on a Nikon Ti-E inverted microscope equipped with a Hamamatsu ORCA-Flash 4.0 V2 cMOS camera, motorized stage and maintained in focus using Nikon Perfect Focus System. For each drug treatment, two large composite images of 8×8 fields of view were generated by digital stitching using Nikon Elements. To quantify EVL levels, a binary mask was generated against F-actin staining using Nikon Threshold Module and EVL signal was quantified within this mask.

RNA-Seq Analysis.

mRNA expression in breast cancer was analyzed in The Cancer Genome Atlas (TCGA) breast cancer RNA-sequencing (RNA-seq) dataset. RNASeq Version 2 level 3 data were downloaded from TCGA breast cancer; 1062 breast tumors and 113 normal tissue samples were included in the analysis. Tumor samples were classified as ER+ or ER− based on the ER status indicated in the accompanying clinical report. Fold-change was computed manually using R as well as via bioconductor package, DESeq2. Raw counts from level 3 data, which includes non-integer numbers, were rounded off for analysis in DESeq2, which requires integer based read counts. P-value was calculated using paired t-test for manual calculation and Benjamini-Hochberg method was used for multiple test corrections. The bioconductor package, pheatmap3, was used to plot heat maps using row scaling on gene counts and clustering was enabled for gene clustering.

Chromatin Immunoprecipitation Assay.

Experiments were performed as described previously (Carroll, J. S. et al. Cell 122, 33-43 (2005)). Briefly, Prior to the assay, cells were hormone-starved for three days in phenol-free DMEM base media supplemented with 10% charcoal-stripped FBS. Starved cells were treated for 45 min with estradiol (10 nM). For chromatin Immunoprecipitation (ChIP), chromatin was cross-linked with 1% paraformaldehyde (PFA; Electron Microscopy Sciences) for 8 min at room temperature. PFA was then quenched using 125 mM glycine and 5 mg/mL Bovine Serum Albumin (BSA). Cells were scraped with PBS and cellular pellets were isolated by centrifugation at 2000 rpm for 5 min at 4° C. Pellets were resuspended in lysis buffer (1% SDS, 10 mM EDTA and 50 mM Tris pH 8.0) and sonicated using an E210 instrument (Covaris) to an average size of 350 bp according to manufacturer's protocol. After clearing by centrifugation at 15000 rpm for 15 min, 5 µl of sample was collected as input before immunoprecipitation, and the rest was diluted 5-fold in dilution buffer (20 mM Tris pH 8.0, 150 mM NaCl, 2 mM EDTA, and 1% Triton X-100). Chromatin complexes were immunoprecipitated by an overnight incubation at 4° C. with 2 µg anti-ER antibodies (Santa Cruz, HC-20 and Thermo-Fisher, AB-10), followed by a 45 min incubation with 40 µl 1:1 mix of protein A and G Dynabeads (Invitrogen). Beads were then washed four times with RIPA lysis buffer (50 mM Hepes, 1 mM EDTA, 0.7% deoxycholate, 1% NP-40 and 0.5M LiCl) and twice with Tris-EDTA (TE) buffer. The protein/DNA complexes were eluted in 1% SDS, 0.1M sodium bicarbonate buffer heated at 65° C. for 6 hours to reverse the PFA cross-linking. DNA was isolated using PCR cleanup kit (Qiagen) and quantitated using Quant-IT per manufacturer's instructions (Thermo-Scientific). DNA fragments were analyzed by qPCR using SYBR green master mix (Kapa Biosciences) on an ABI 7300 instrument (Applied Biosystems). For ChIP-Seq, purified DNA was then end repaired and ligated to adapter oligos (Illumina) and amplified. Sequencing was performed at the Center for Cancer Computational Biology at Dana Farber Cancer Institute using an Illumina HISEQ2000 instrument. Reads were mapped to the human genome using STAR and peaks indicating ER binding were called comparing ChIP and corresponding Chromatin Input libraries using MACS2.1 and a threshold of $p<10-5$. ChIP-seq SPMR traces were generated using MACS2.1 followed by conversion to Big-Wig format using the bedGraphToBigWig tool. High confidence binding cutoff was arbitrarily chosen at $q<10-200$ and presence in both ChIP-Seq replicates corresponding to approximately 10% of the entire dataset.

Quantitative Real-Time PCR.

Cells were treated for 24 hours with estradiol (10 nM), tamoxifen (1 µm), or fulvestrant (100 nM); estradiol treated cells were hormone-starved for 24 hours as described above. Total RNA was isolated using Isolate II RNA kit (Bioline) and cDNA was then synthesized from 1ug of RNA using XLA script cDNA kit (Quanta BioSciences). SYBR green PCR mix (Apex) was used for Real Time qPCR on the ABI Fast 7500 system. Samples were run in triplicates in each experiment and relative mRNA levels were normalized to GAPDH.

Western Blot Analysis.

Cells were scraped on ice in lysis buffer (10% glycerol, 1% IGEPAL, 50 mM Tris pH7.5, 200 mM NaCl, 2 mM MgCl2, protease inhibitor cocktail from Proteomics, M250-1 ML, and phosphatase inhibitor cocktail from Boston BioProducts, BP479). Lysates were incubated on ice for 15 min followed by clarification at 14000 rpm for 15 min at 4° C. Protein concentrations were measured using Bradford assay (Thermo) and 25 µg total protein from each sample were resolved by SDS-PAGE on 10% polyacrylamide gels. Samples were transferred onto polyvinylidene difluoride (PVDF) membranes (Millipore), which were blocked overnight in 5% BSA at 4° C., then probed with polyclonal rabbit anti-EVL antibody (a gift from Frank Gertler) at 1:2000 dilution, overnight at 4° C., followed by standard western blotting protocol. Goat anti-rabbit or anti-mouse horseradish peroxidase secondary antibodies (Thermo-Fisher) used with Enhanced Chemi-Luminescence (ECL, BioRad Clarity Western ECL Substrate, 170-5061), or near-infrared fluorescent (Licor) secondary antibodies were used for detection. To re-probe following ECL western blotting, antibodies were stripped in 0.2M NaOH for 15 min at room temperature, and membranes were re-probed for actin, as a loading control, using antiactin antibody (abcam, ab3280, 1:1000) and developed following the same western blot protocol.

CRISPR/Cas9 Knock-in.

Cells were edited using the CRISPR/Cas9 as previously described (Chou, Y.-Y. et al. Identification and Characterization of a Novel Broad-Spectrum Virus Entry Inhibitor. J. Virol. 90, 4494-4510 (2016)). Briefly, the three following constructs were co-transfected to edit endogenous EVL: 1) a plasmid coding for the SpCas9 endonuclease; 2) a template plasmid coding for the sequence of eGFP and a flexible linker with an amino acid sequence of GGSGGSGGS (SEQ ID NO: 3) flanked upstream and downstream by ~800 bp of the ATG codon of EVL; and 3) a linear double-stranded DNA product obtained by PCR amplification and purification coding for the U6 promoter, the gRNA targeting the ATG region of the EVL gene and the tracrRNA recognized by Cas9. The gRNA sequence was ACTTTTCAGC-CATGGCCACA (SEQ ID NO: 4), the underlined nucleotides representing the start codon of the EVL gene. Edited cells (eGFP-EVLedited) were generated by transfection, at 70% confluence, with 600 ng of each of the above-mentioned constructs using FUGENE HD transfection reagent in OptiMEM. Edited cells were enriched by fluorescence-activated cell sorting (FACS) on a FACSAria II and efficient editing of EVL was verified by fluorescence microscopy and validated by genomic PCR.

Laser Scanning Confocal Microscopy.

Cells were embedded in a 3D type-I collagen matrix in 8-well glass-bottom chamber slides as previously described in Three-Dimensional Culture System methods above. Cells were imaged using a 60× Plan Apo 1.42 NA Olympus Objective on an Olympus Fluoview1200 laser scanning confocal microscope. Images are maximum intensity projections of confocal z-series.

DCIS Mouse Model.

A previously described protocol of intraductal injection was followed with modifications (Behbod, F. et al. Breast Cancer Res. 11, R66 (2009); Sflomos, G. et al. Cancer Cell 29, 407-422 (2016)). In brief, eight-week-old female NOD/SCID mice were ovariectomized and implanted with a sub-dermal 90-day release 0.72 mg estradiol pellets (Innovative Research of America). Two days after implantation, $1 \times 10^4$ cells suspended in 3 µl growth media were injected into the primary mammary duct through a cleaved nipple, using a Hamilton syringe. For the first experiment, MCF7 cells expressing shRNA targeting EVL and control cells expressing the LKO vector control were used; for the second experiment, cells expressing an inducible form of shRNA targeting EVL and TRIPZ vector control were used. After 6-8 weeks, tumors were harvested, fixed in 4% PFA (Electron Microscopy Sciences) and processed for tissue staining. For experiments with cells expressing an inducible TRIPZ constructs, doxycycline was administered in the drinking water at a concentration of 2 mg/mL for 2 weeks before tumor harvesting.

Example 2

ER Expression is Associated with Low Dissemination of Breast Cancer Cells

Figure 8:
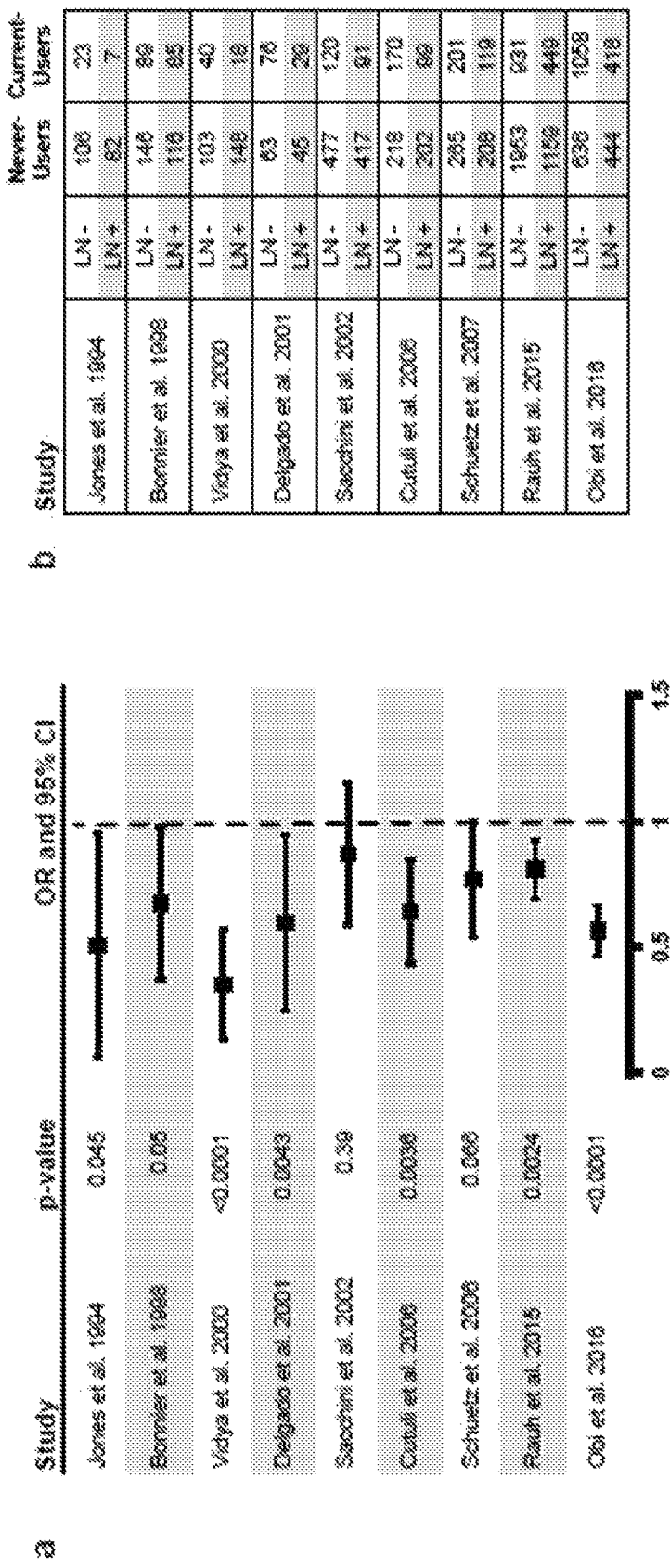
FIG. 8. (a) Binary assessment of LN dissemination (LN+ vs LN−). Forest plot showing Odds Ratio, with 95% Confidence Interval (OR, 95% CI) of LN positivity in current-users compared with never-users of HRT. (b) Number of current-users and never-users with either LN− or LN+ tumors in the studies analyzed in (a). (c) Kaplan-Meier plot showing survival of ER+ breast cancer patients clustered by LN status as LN≤3 and LN>3; $p<0.001$ (Chi-square test). (d) Kaplan-Meier plot showing survival of ER+ breast cancer patients clustered by LN status as LN− and LN+; $p<0.001$ (Chi-square test). ER levels are 1.5× higher in LN+. (e) Scatter plot showing quantification of positive LN in Low (≤7 μm) and High (≥9 μm) LII tumors from NCI BCP TMA (TMA #1); values are mean±s.d.; *$p=0.03$ (Mann-Whitney exact t-test). (f) Scatter plot showing quantification of positive LN in tumors with Low (≤7 μm) and High (≥9 μm) LII tumors from Cedar-Sinai LumB TMA (TMA #2); values are mean±s.d.; *$p=0.01$ (Mann-Whitney exact t-test). (g) Kaplan-Meier plot showing survival of Luminal B ER+ breast cancer patients clustered by ESR1 expression as ESR1 HIGH (3rd quartile) and ESR1 LOW (1st quartile); $p<0.05$ (Chi-square test). (h) Quantification of proliferation of MCF7 cells treated with respective drugs for 48 hours. Fold change in proliferation is shown between treatments.
Figure 8:
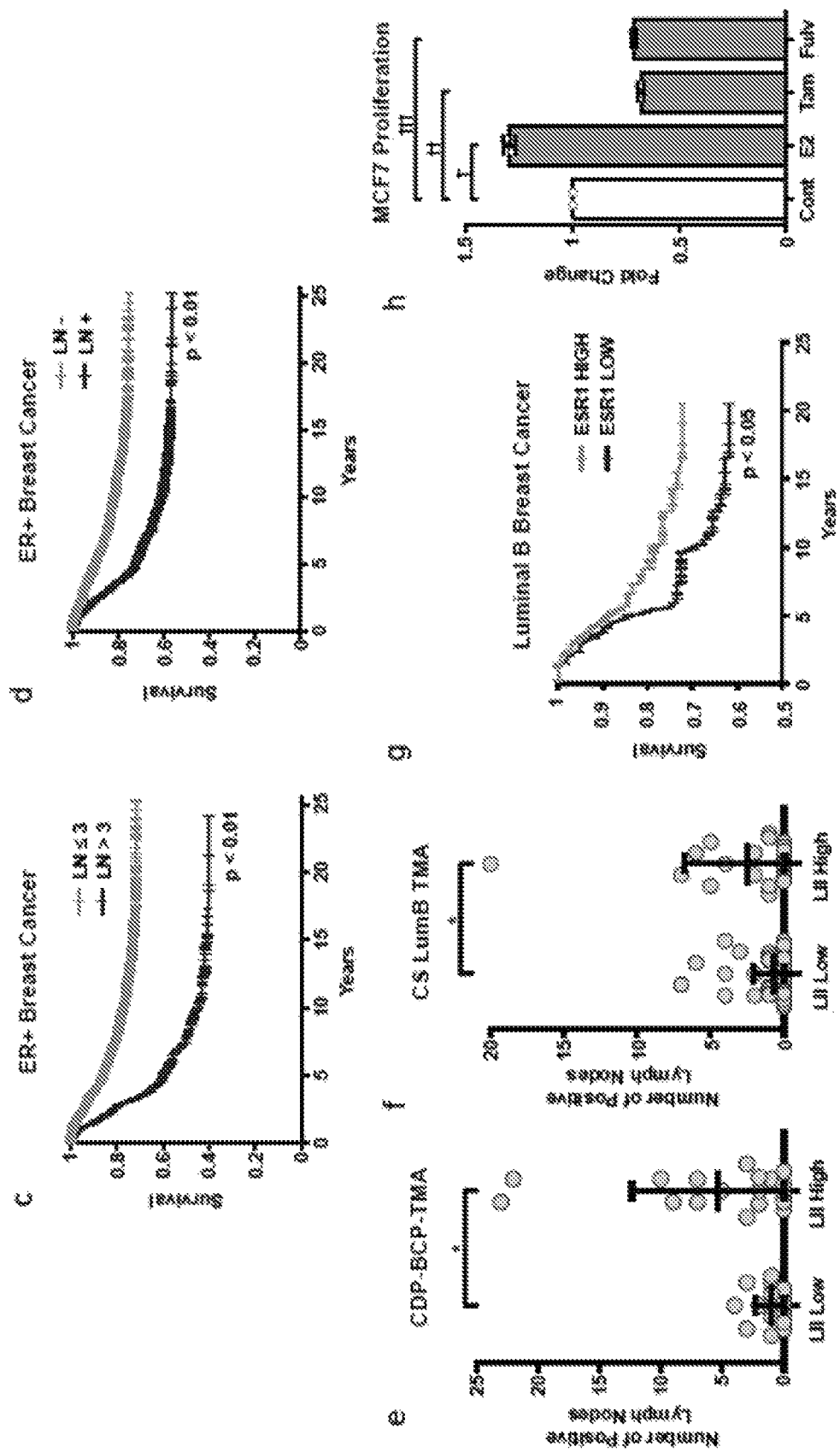

In a meta-analysis of ten epidemiological studies (Czernichow, supra; Jones et al., supra; Bonnier et al., supra; Delgado et al., supra; Vidya, supra; Sacchini et al., supra; Cutuli et al., supra; Schuetz et al. supra; Rauh et al., supra; Obi et al., supra), lymph node (LN) positivity was investigated in postmenopausal women diagnosed with breast cancer while on HRT (current-users), compared to women who never used HRT (never-users). LN status was used as a metric of tumor cell dissemination and the commonly-used cutoff of >3 (LN>3) as a marker of distant metastasis beyond the regional axillary lymph nodes. HRT was associated with lower odds ratio (OR) of having LN>3, indicating less distant dissemination (FIGS. 1a and 1b). Moreover, to examine both regional and distant dissemination, a binary assessment of LN status (LN+ or LN−) was performed. This analysis showed that OR of having LN+ was lower in HRT current-users, indicating less regional and distant dissemination. In addition, in ER+ breast cancer, tumors with low LN dissemination had higher ER levels, as compared to tumors with high LN dissemination (1.8-fold in LN≤3 and 1.5-fold in LN−, compared to LN>3 and LN+, respectively); patients with less LN-disseminated tumors have higher survival rate (FIGS. 8c and d).

The effect of ER on cancer cell invasion, the initial step in metastatic dissemination, was investigated in breast cancer patient samples from two Tissue Microarrays (TMA #1 and TMA #2; see Methods). The Local Invasion Index (LII) was determined for each tumor sample by employing the nearest neighbor distance (NND) approach, typically used in spatial analysis to study the second-order effect or local variation of point patterns (Gatrell, A. C., et al. Transactions of the Institute of British Geographers 21, 256 (1996)). Treating cancer cells (identified by cytokeratin positivity) as stochastic events in a point pattern analysis, the distance between the nucleus of each cell and the nucleus of its most proximal neighboring cell (NND) was measured and LII was calculated as the average NND within each tumor sample (FIGS. 1c and 1d).

In TMA #1, 64 samples were analyzed from ER+ and ER− tumors, exhibiting a wide range of LN dissemination. Compared to the more aggressive ER− tumors, ER+ tumors exhibited significantly lower LII (FIGS. 1e and 1f), indicating that ER positivity is associated with lower invasion rate. Moreover, tumors with LII≤7 μm (denoted as LII low) were associated with 5-fold less LN dissemination than tumors with LII≥9 μm (denoted as LII high) (FIG. 8e), indicating that, in addition to ER positivity, low local invasion corresponds to low distant LN dissemination. These data indicate that local invasion is a valid parameter to assess dissemination.

Furthermore, the association between ER expression and invasion in TMA #2, which comprised samples from ER+ luminal B tumors was investigated. Among ER+ tumors, luminal B tumors disseminate more extensively and exhibit a wide range of ER expression levels (Hague, R. et al. Biomarkers Prev. 21, 1848-1855 (2012)). Quantitative analysis of ER levels (average intensity of ER immunofluorescence in each tumor sample) and LII in 180 samples from TMA #2 revealed a significant negative linear correlation between ER expression and invasion (FIG. 1g-i). In addition to expressing higher ER, low LII tumors are associated with less LN dissemination as compared to high LII tumors (FIG. 8f). Moreover, analysis of survival rates in a cohort of patients with luminal B tumors (Curtis, C. et al. Nature 486, 346-352 (2012)) shows that high ER is associated with better outcome (FIG. 8g). Together, these data demonstrate that in luminal B breast cancer, tumors with high ER expression exhibit low dissemination and are less invasive.

To investigate the direct effect of altering ER activity on invasion, an in vitro culture system to quantify the level of invasion of ER+ MCF7 breast cancer cells into 3D matrix under estradiol (E2) or ER inhibitor treatment was developed (FIG. 1j). It was found that ER inhibition enhanced invasion of MCF7 cells, whereas E2 suppressed it (FIGS. 1k and 1l). These results are consistent with previous reports of ER suppressing invasiveness of breast cancer cells (Platet, N., et al. Crit. Rev. Oncol. Hematol. 51, 55-67 (2004); Gao, Y. et al. Nature Communications 8, 14483 (2017)). Conversely, ER inhibition suppressed proliferation of the cells, whereas E2 promoted proliferation (FIG. 8h). Together, these results demonstrate that the observed changes in invasion upon altering ER activity are not the result of changes in the proliferation rate but are rather induced by enhanced cell motility.

Example 3

ER Mediated Actin Cytoskeletal Remodeling Induces Suppressive Cortical Actin Bundles (SCABs)

Figure 2:
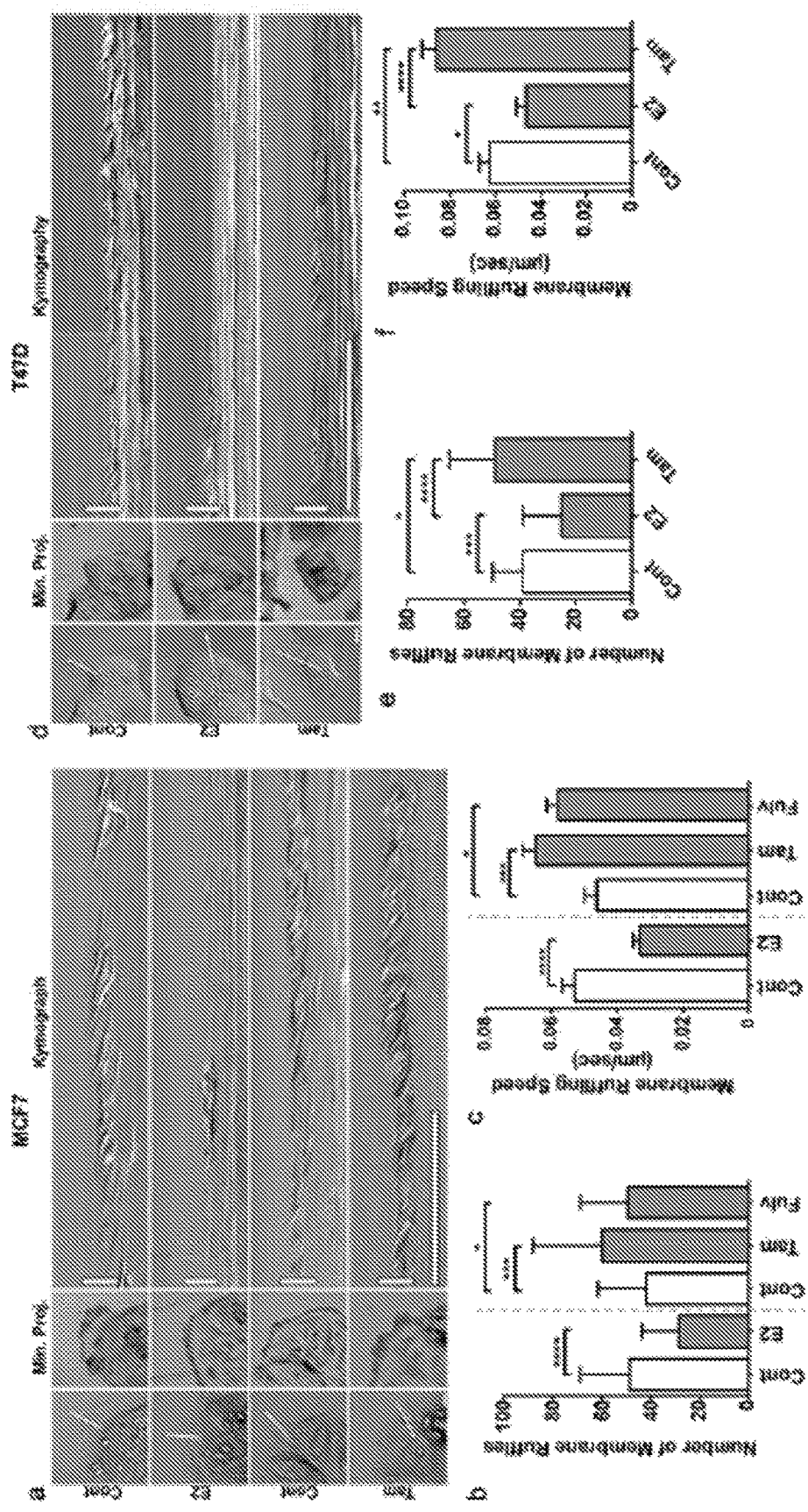
FIG. 2. ER mediated actin cytoskeletal remodeling induces suppressive cortical actin bundles (SCABs). Quantification of Protrusive Activity: (a) Leading edge kymography in representative time-lapse movies of control and E2-treated MCF7 cells (cultured under hormone-starvation conditions), and control and ER-inhibited cells (cultured in regular media). Left panels show corresponding images from the time-lapse movies. (b) Membrane ruffle quantification. (c) Ruffling speed quantification. (d) Leading edge kymography in representative time-lapse movies of T47D cells. (e) Membrane ruffle quantification. (f) Ruffling speed quantification. Volumetric Analysis of Leading Edge Actin: (g) Illustrative confocal z-series (0.2 µm z-step), and corresponding 3D binary mask used to quantify average fluorescence intensities of Arp2/3 and pMLC in the area within 3 µm of the cell edge. (h) Maximum intensity projections of z-series of E2 or fulv treated MCF7 cells, and 3D reconstructions of boxed areas. (i) Quantification of leading edge Arp2/3 and pMLC in MCF7 cells. (j) Maximum intensity projections of z-series of E2 or tam treated T47D cells and corresponding 3D reconstructions of boxed areas. (k) Quantification of leading edge Arp2/3 and pMLC in T47D cells.
Figure 2:
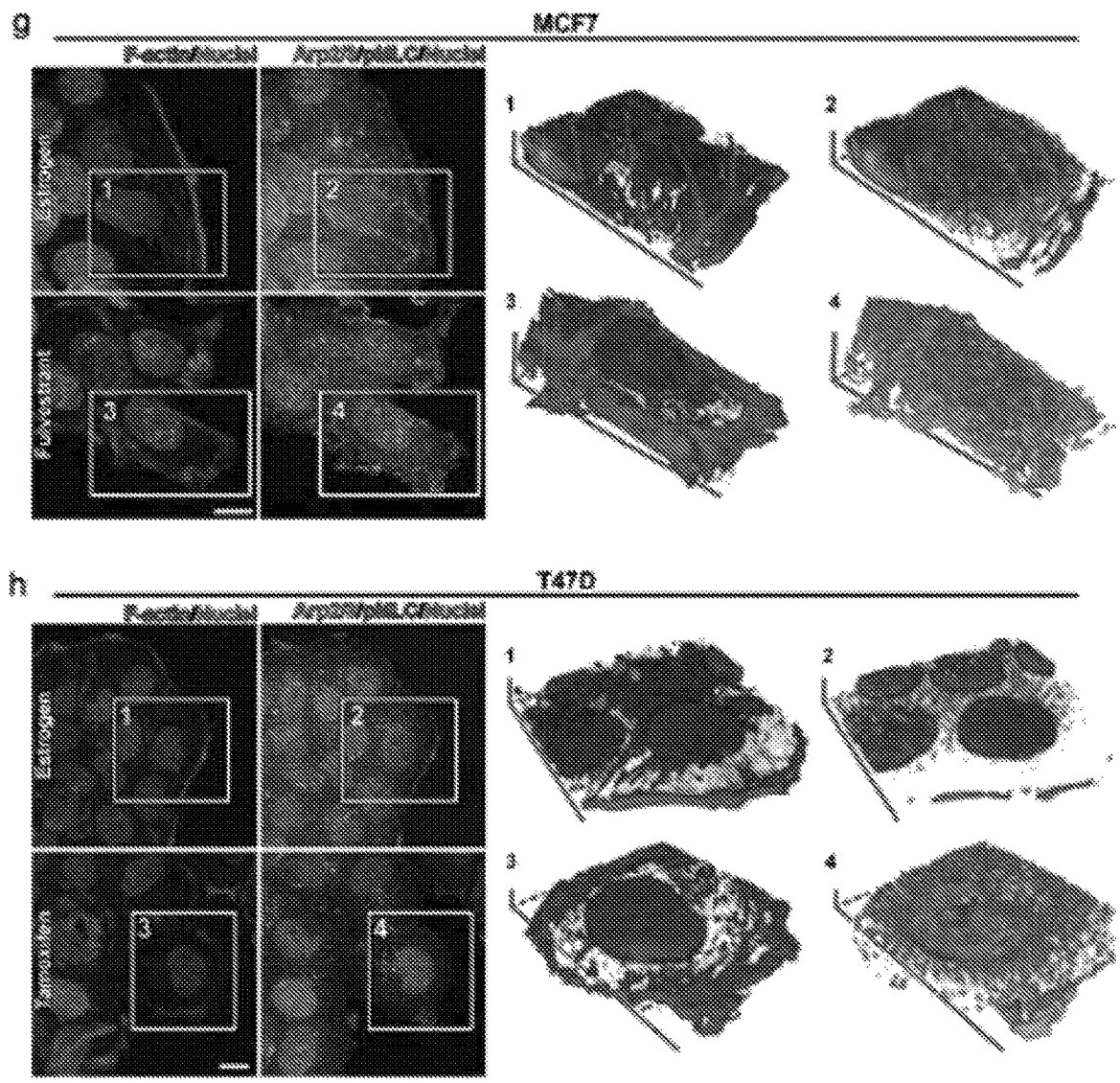
Figure 2:
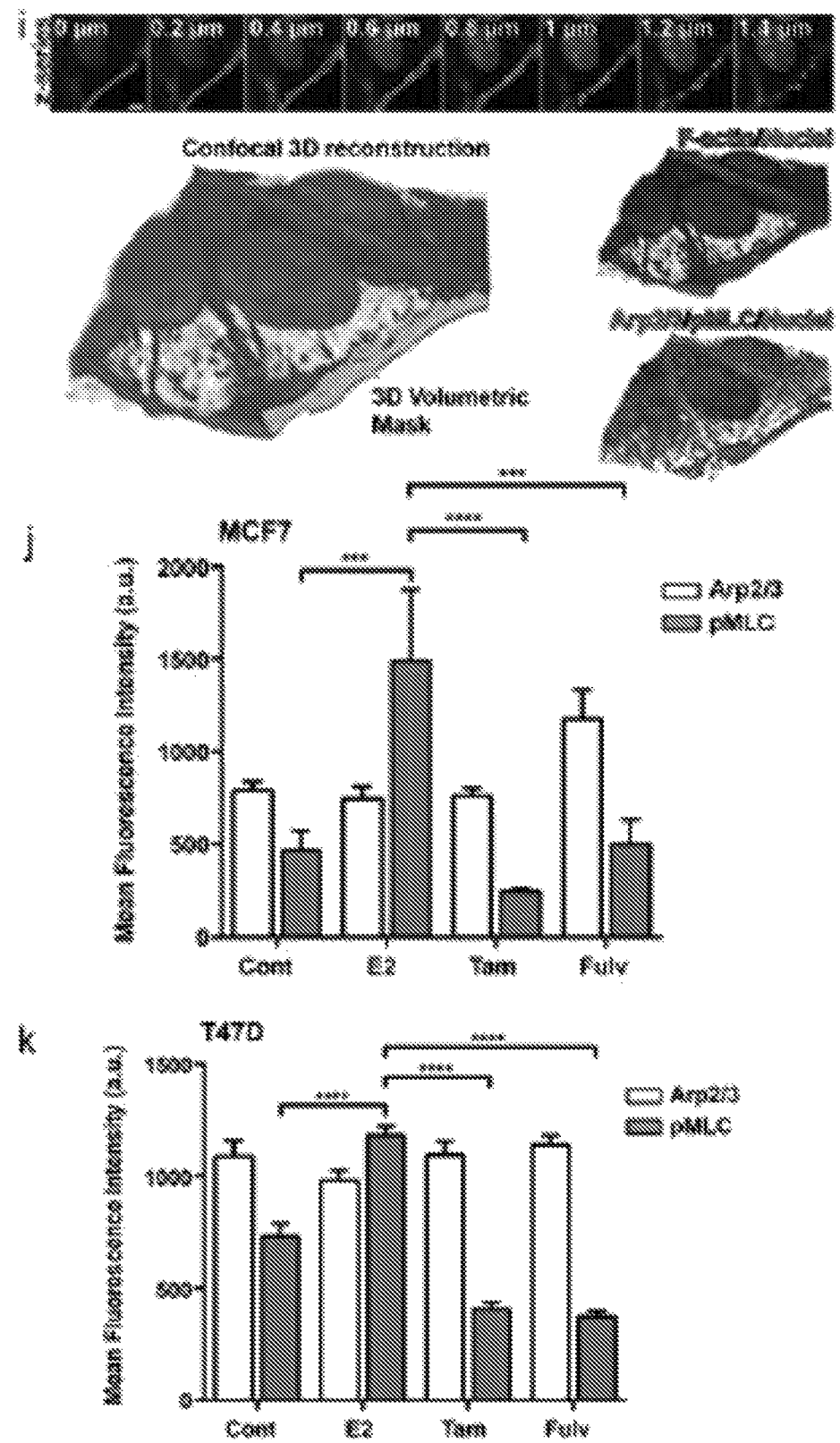

Using kymography analysis, the motility dynamics of membrane protrusion, which is crucial for cancer cell invasion, was quantitated (Meyer, A. S. et al. J. Cell Biol. 197, 721-729 (2012)). This analysis showed a marked decrease in the number and speed of membrane ruffles in E2-treated MCF7 cells, as compared to control (FIG. 2a-c). Conversely, protrusive activity was significantly enhanced at the leading edge of MCF7 cells treated with ER inhibitors (FIG. 2a-c). These data were validated in ER+ breast cancer T47D cells (FIG. 2d-f). Mechanistically, enhanced motility dynamics are well-established characteristics of an aggressive invasive behavior (Bravo-Cordero et al. Curr. Opin. Cell Biol. 24, 277-283 (2012)); therefore, the suppression of protrusive activity by ER is in line with the low dissemination of tumor cells with high ER expression.

Figure 9:
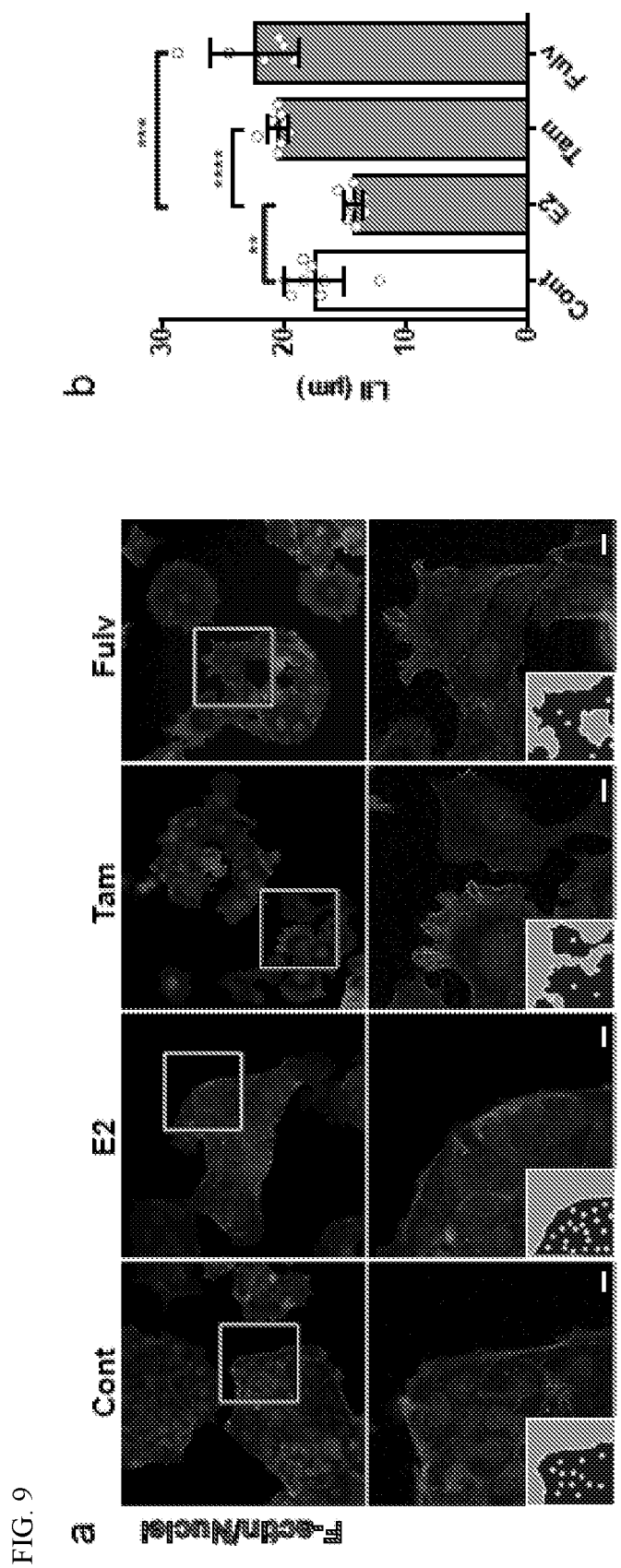
FIG. 9. (a) F-actin staining of MCF7 cells after corresponding treatments. Lower panels are magnifications of boxed areas. Insets are binary masks of actin stain (black) and nuclei. Scale bar is 10 μm. (b) Quantification of LII across treatment groups.

Motility dynamics of membrane protrusions are regulated by the architecture of the actin cytoskeleton (Bravo-Cordero et al., supra). Examining actin cytoskeletal remodeling by ER, it was found that E2-treated MCF7 cells exhibited prominent cortical actin bundles, which were concurrent with the absence of protrusions. Conversely, ER inhibition diminished these bundles and enhanced cell scattering and dissemination (FIGS. 9a and b). Similar actin bundles have been previously observed in normal cells, where they constitute a contractile cortical barrier that suppresses Arp2/3-mediated protrusions (Lomakin, A. J. et al. Nat. Cell Biol. 17, 1435-1445 (2015); Fischer, R. S., et al., Curr. Biol. 19, 260-265 (2009)). The levels of phosphorylated Myosin Light Chain (pMLC) were quantitated as a contractility marker (Vicente-Manzanares et al., J. Cell Biol. 176, 573-580 (2007)), and of Arp2/3 at the leading edge after altering ER activity in ER+ breast cancer cells. Considering the 3D morphometric properties of cortical bundles and protrusive ruffles, volumetric analysis of fluorescence intensity was used in confocal z-series (FIG. 2g). E2 treatment significantly increased pMLC at cortical bundles, demonstrating elevated contractility, which was suppressed by ER inhibition (FIGS. 2h and 2i). The decrease in cortical contractility coincided with Arp2/3-positive leading edge ruffles; however, no significant changes in Arp2/3 levels at the leading edge were detected, indicating other actin regulators could be driving protrusion under ER inhibition (FIG. 2i). These data were confirmed in T47D cells (FIGS. 2j and 2k). These results indicate that the suppressive effects of ER are mediated through remodeling of the actin cytoskeleton to generate Suppressive Cortical Actin Bundles (SCABs).

Example 4

Figure 3:
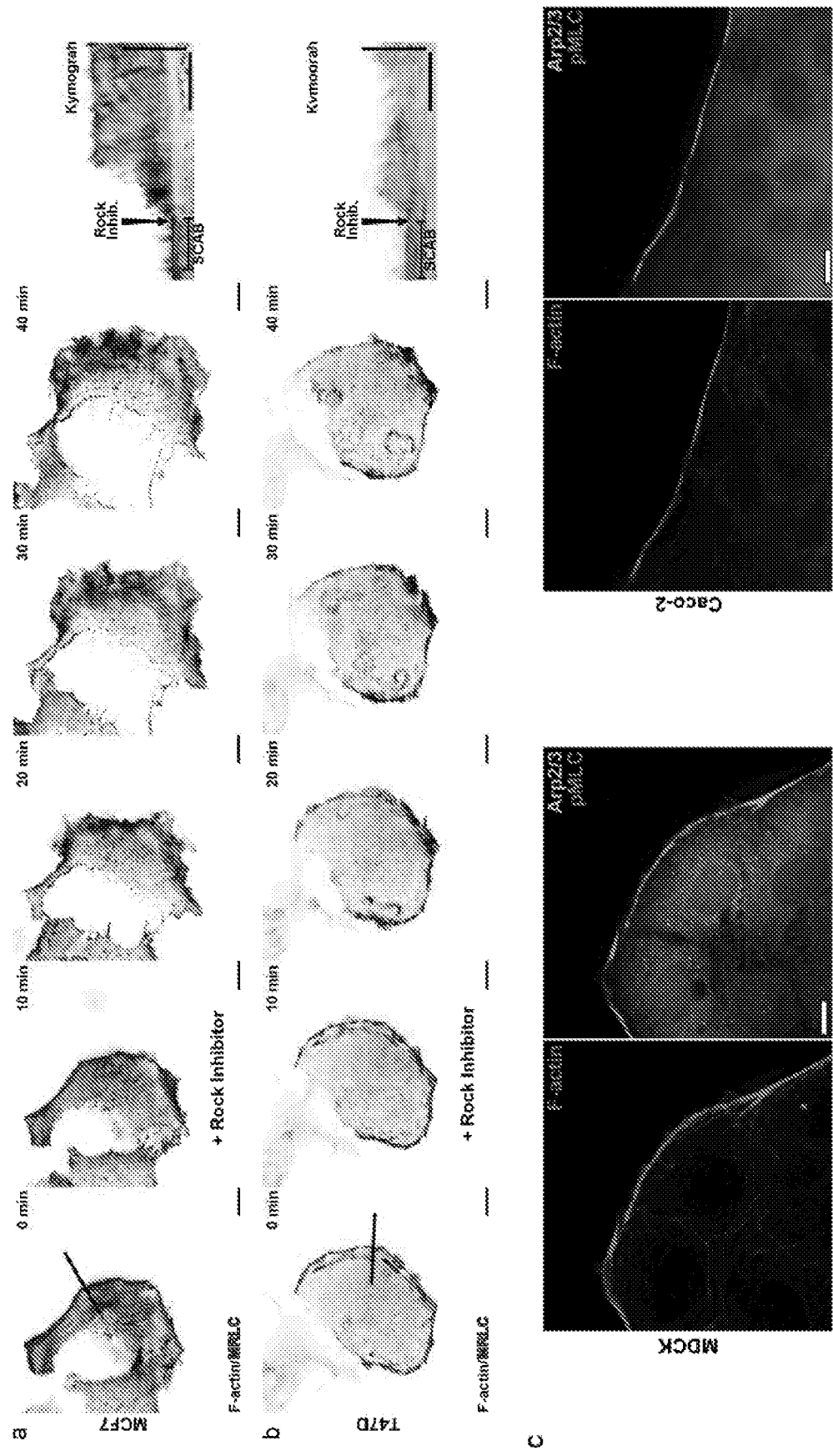
FIG. 3. SCABs suppress leading edge motility in a myosin contractility dependent manner. (a) Leading edge kymography in MCF7 cells (top row) and T47D cells (bottom row) expressing iRFP-Lifeact (black) and MLC-mRuby2 before and after dissolving SCABs using 25 uM ROCK inhibitor. Left panels are images from TIRF microscopy time-lapse series before and after addition of ROCK inhibitor. Right panel shows MLC kymograph (denoting SCABs) superimposed over Lifeact kymograph (demarcating the leading edge). (b) Immunofluorescence of SCAB in MDCK canine kidney epithelial cells and Caco-2 human intestinal epithelial cells. (c) Leading edge kymography in MDCK cells (top row) and Caco-2 (bottom row) cells expressing iRFP-Lifeact (black) and MLC-mRuby2 before and after dissolving SCABs using 25 µM ROCK inhibitor. Right panel shows MLC kymograph (denoting SCABs) superimposed over Lifeact kymograph (demarcating the leading edge (d) the dissolution of SCABs increased the motility dynamics of the leading edge in MDCK canine kidney epithelial cells and (e) Caco-2 human intestinal epithelial cells.
Figure 3:
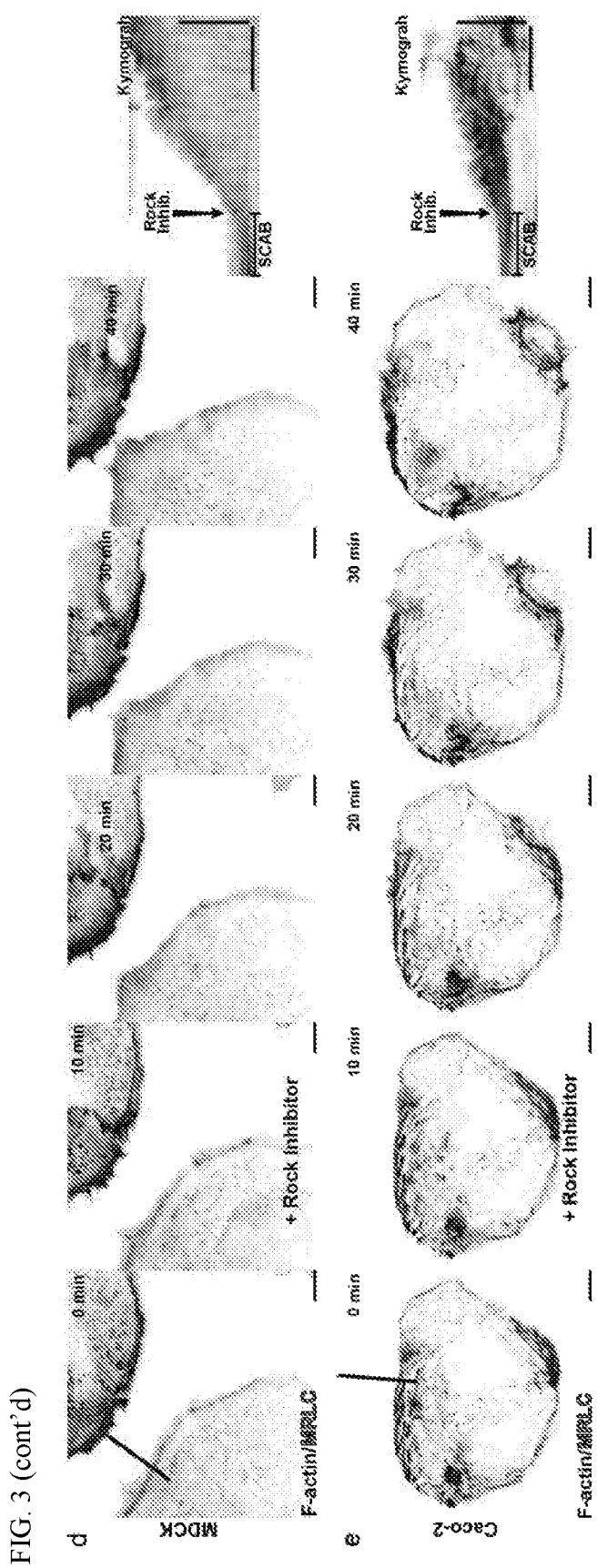

SCABs Suppress Leading Edge Motility in a Myosin Contractility Dependent Manner The relationship between cortical contractility and membrane motility dynamics was further examined. Using live-cell Total Internal Reflection Fluorescence Microscopy (TIRFM), SCABs at the leading edge of MCF7 and T47D cells were imaged before and after inhibiting contractility using the ROCK inhibitor, Y-27632; the actin cytoskeleton was labeled with iRFP-Lifeact, and SCABs with MLC-mRuby2. Inhibiting contractility resulted in the loss of MLC at the leading edge and the dissolution of SCABs, and led to a rapid increase in protrusive activity, revealing a direct relationship between SCABs and the suppression of membrane motility dynamics (FIGS. 3a and 3b). In addition, the existence of SCABs, their contractile nature, and their suppressive effects were validated in two types of epithelial cells: MDCK canine kidney epithelial cells, and Caco-2 human intestinal epithelial cells (FIGS. 3c and 3d). Staining for pMLC in these cells revealed the contractile nature of these cortical structures, which corresponded with the absence of membrane protrusions (FIG. 3c). Importantly, the dissolution of SCABs dramatically increased the motility dynamics of the leading edge in both epithelial cell types (FIG. 3d). These data indicate that SCABs—and the attenuation of protrusive activity by SCABs—are present not only in ER+ breast cancer cells, but are common features of epithelial cells. ER is potentially enriching for SCABs by inducing the expression of actin regulators that promote SCAB formation.

Example 5

EVL is a Transcriptional Target of ER

Figure 4:
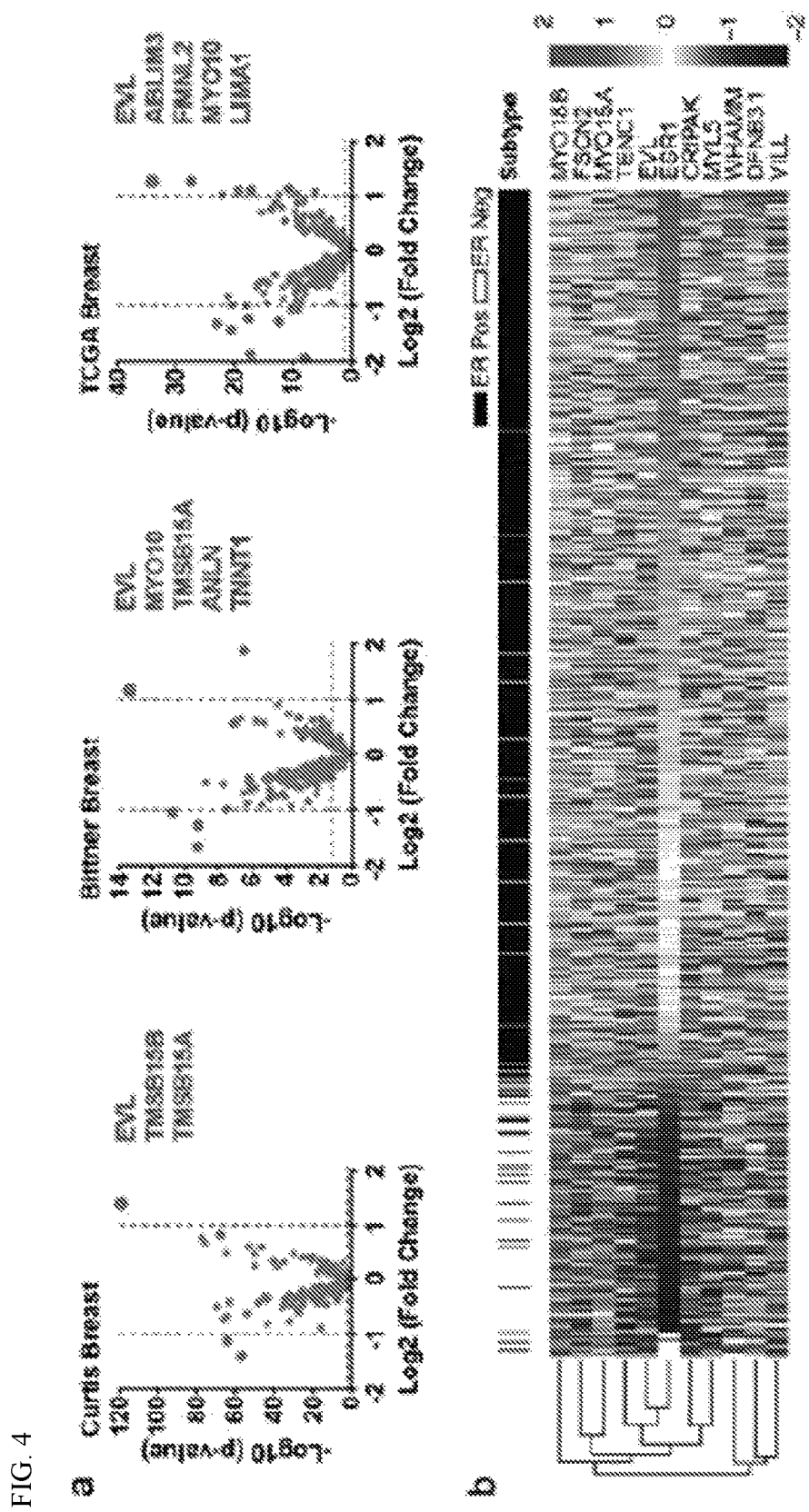
FIG. 4. EVL is a transcriptional target of ER. (a) Volcano plot (significance vs. fold change) showing differential gene expression analysis of actin cytoskeletal regulators between ER+ and ER− breast cancer across multiple studies. Unsupervised Clustering Analysis of TCGA RNA-seq Dataset: (b) Heatmap, generated by row-scaling, showing expression of genes in the ESR1 cluster. Analysis of ER Binding by Chromatin Immunoprecipitation (ChIP). (c) Genomic region surrounding EVL showing ER-ChIP sequencing profile as SPMR (Signal Per Million Reads) trace of two independent ER-ChIP sequencing samples, generated by MACS2.0 and visualized by IGV (Integrative Genomics Viewer). (d) Fold enrichment of ER-binding at 4 peaks found by ChIP-seq, in addition to positive (PGR) and negative controls. Analysis of the Regulation of EVL Expression by ER: (e) qPCR of EVL mRNA in MCF7 cells treated with corresponding drugs for 24 hours, normalized to GAPDH. Fold change shown between treatment groups. (f) Immunolabeling of MCF7 cells after corresponding drug treatment for 72 hours. (g) Quantification of EVL levels in MCF7 cells after treatment with corresponding drugs for 72 hours.
Figure 4:
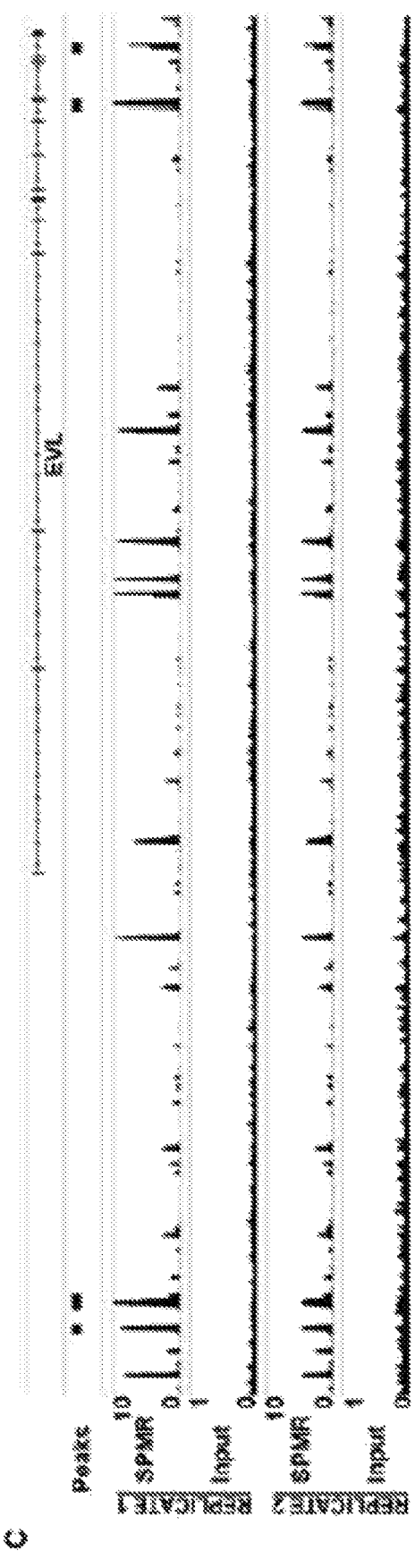
Figure 4:
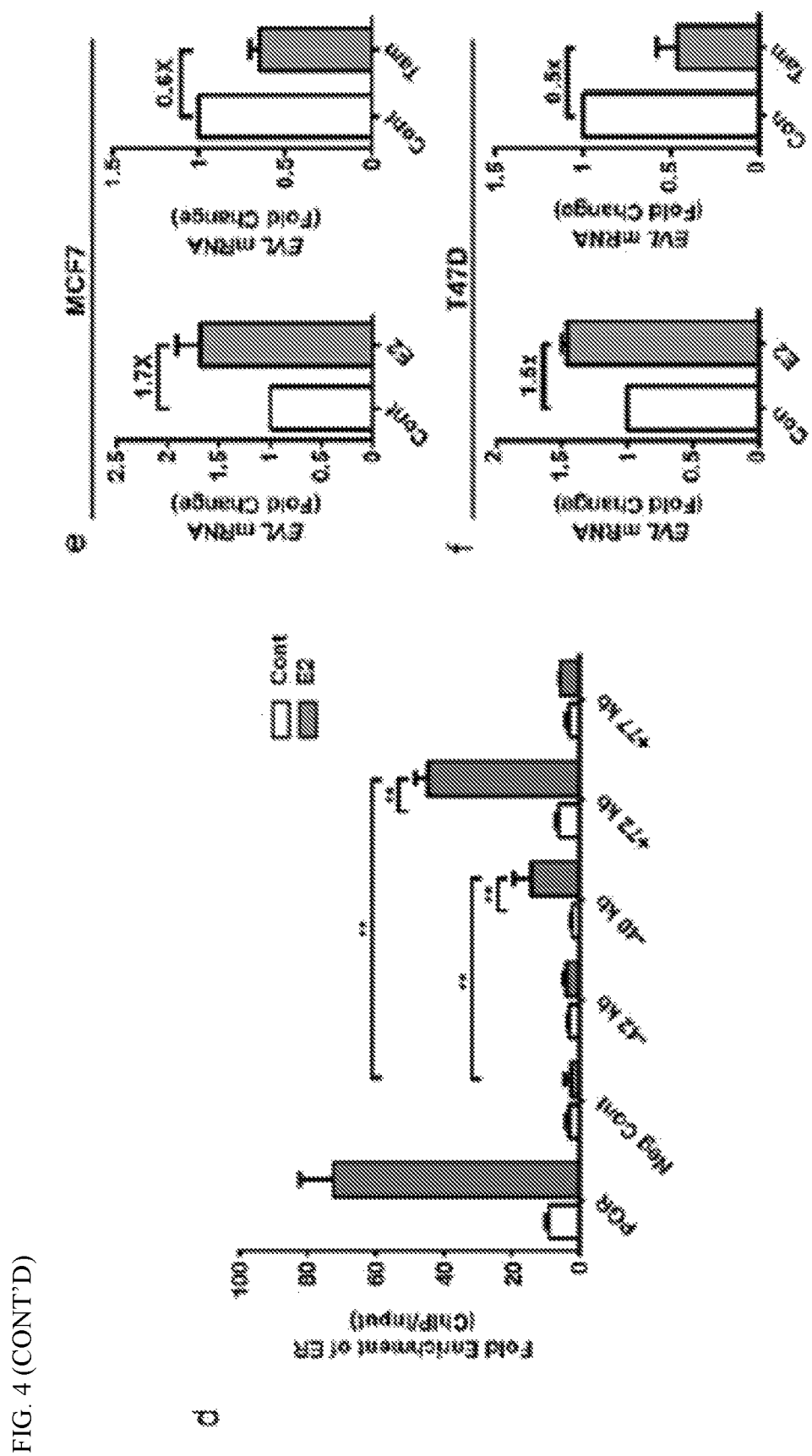
Figure 10:
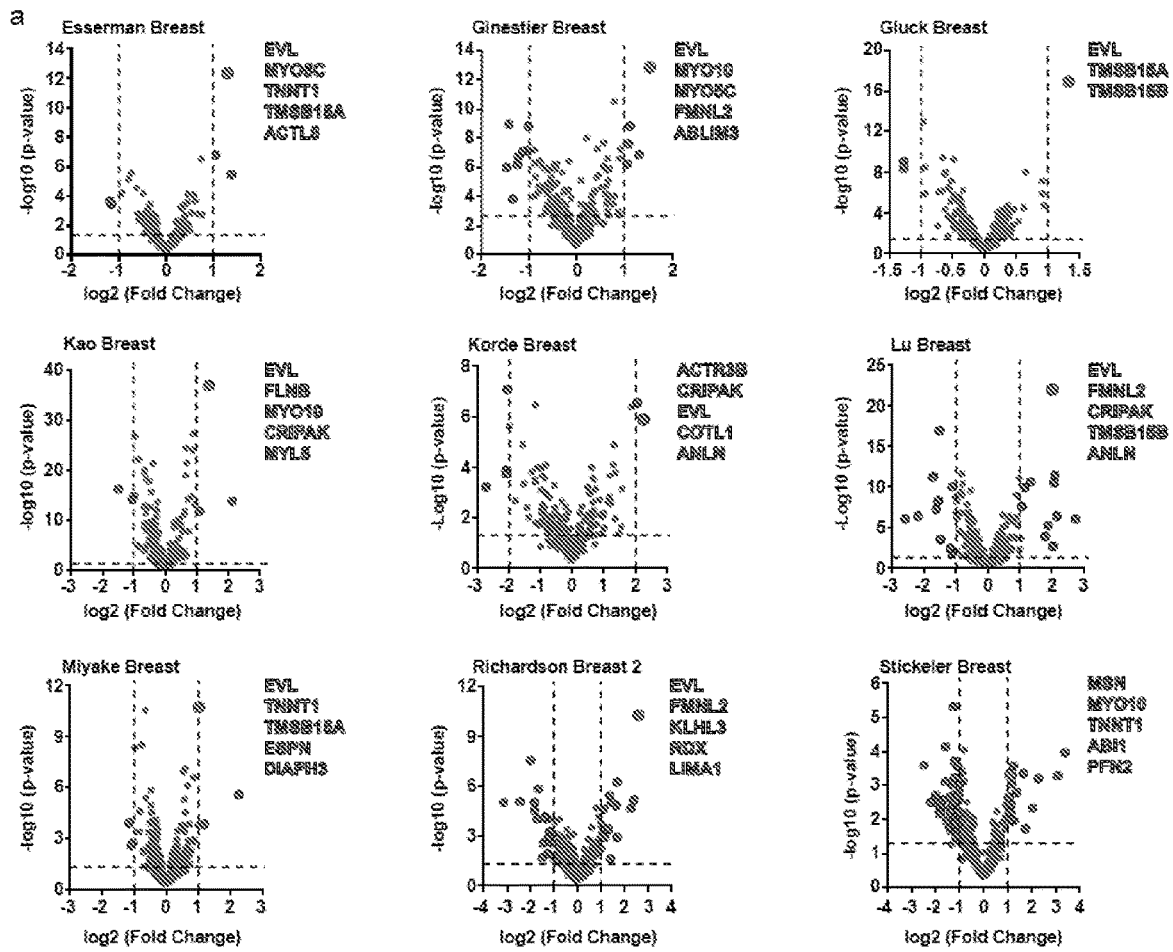
FIG. 10. (a) Differential gene expression analysis of actin cytoskeletal regulators in ER+vs. ER− breast tumors. (b) Volcano plot showing differential transcript levels between ER+ and ER− tumors using the TCGA RNA-seq data set. (c) qPCR of EVL in T47D cells 24 hours post-treatment, normalized to GAPDH.
Figure 10:
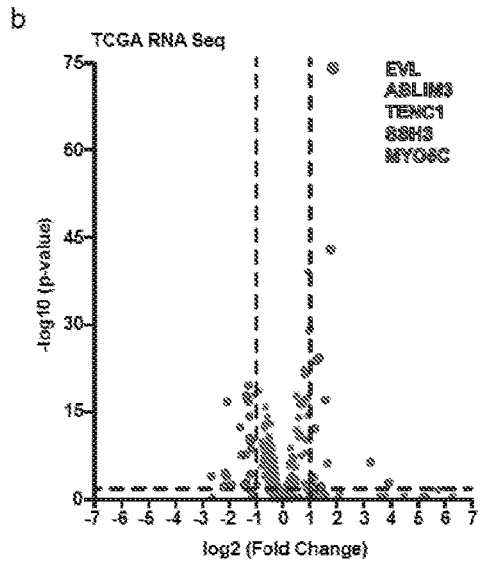
Figure 10:
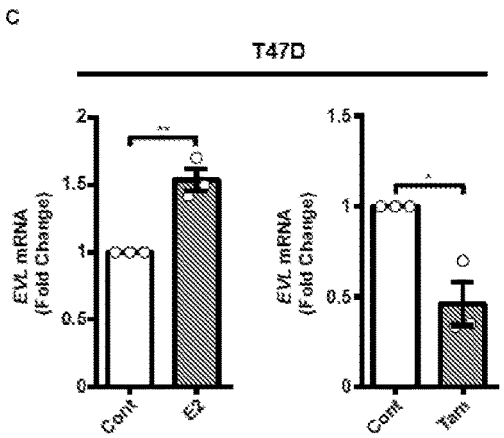
Figure 11:
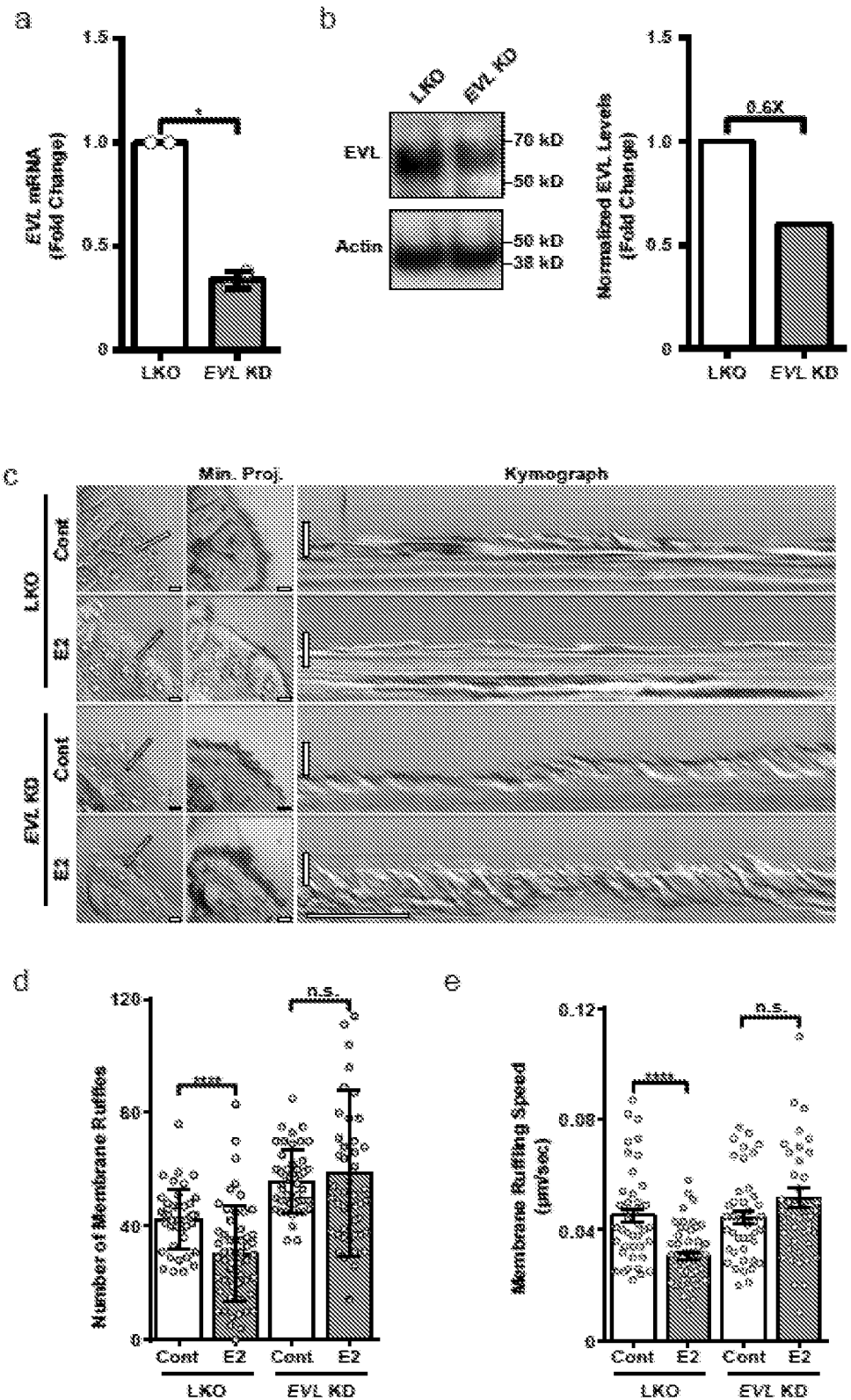
FIG. 11. (a) qPCR of EVL mRNA from LKO and EVL KD MCF7 cells, normalized to GAPDH. (b) Left panel. Western blot of LKO and EVL KD MCF7 cell lysates showing EVL levels and actin loading control. Right panel. Quantification of western blot showing fold change in EVL levels, normalized to actin. (c) Leading edge kymography in representative time-lapse movies of LKO and EVL KD in MCF7 cells treated with vehicle or with E2 for 72 hours. Left panels indicate position at which kymographs were registered (line), and middle panels show minimum intensity projections from the entire time series (Min. Proj.); scale bar is 10 μm. Right panels show corresponding kymographs; (d) Membrane ruffle quantification. (e) Ruffling speed quantification. Data are from three independent experiments, n≥45 per treatment group.
Figure 12:
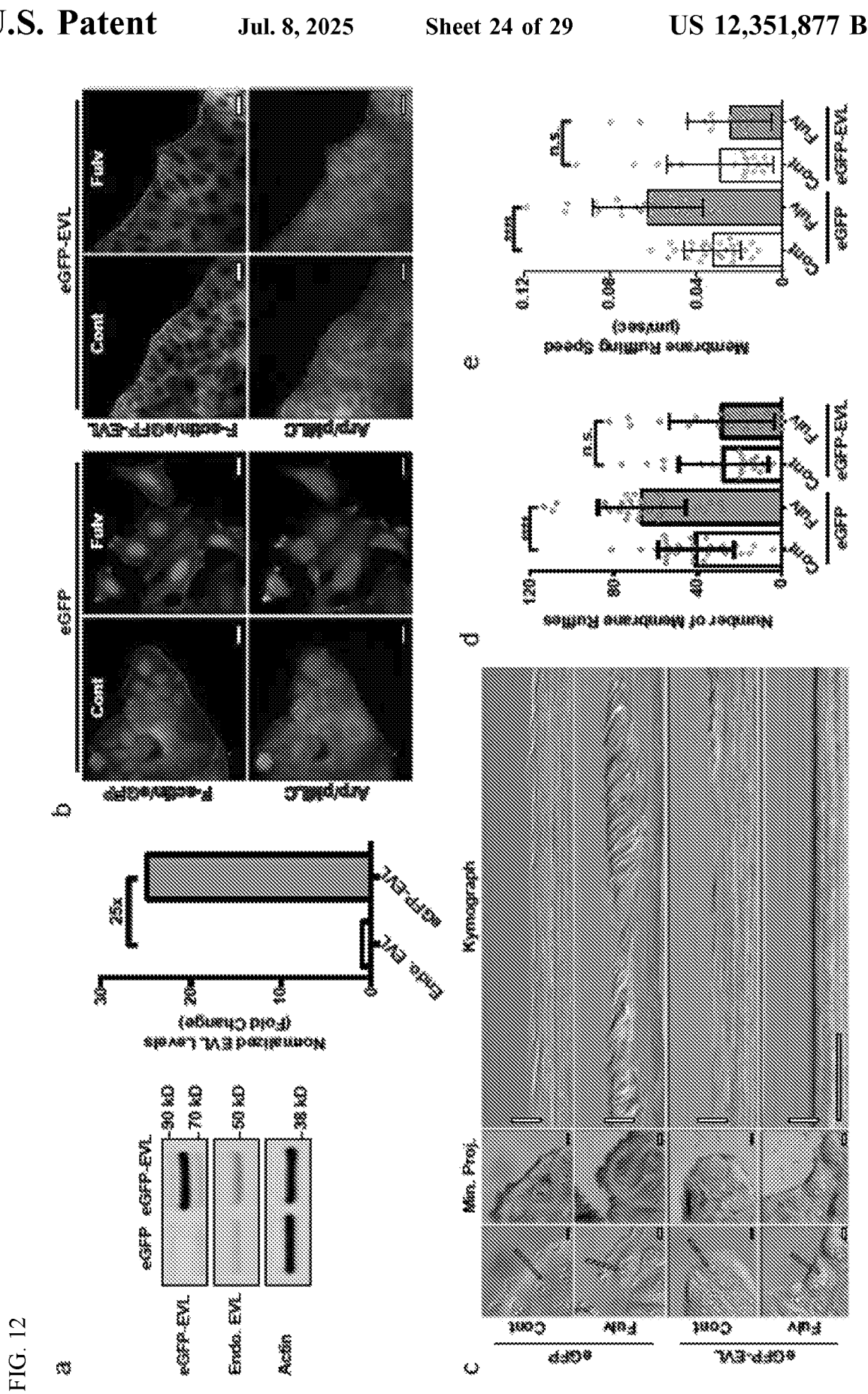
FIG. 12. (a) Left panel. Western blot of eGFP and eGFP-EVL MCF7 cell lysates showing EVL levels and actin loading control. Right panel. Quantification of western blot showing fold change in EVL levels relative to endogenous EVL, normalized to actin. (b) Large composite stitched images of treatment groups in FIG. 5c. (c) Leading edge kymography in representative time-lapse movies of eGFP and eGFP-EVL in MCF7 cells treated with vehicle or with fulv for 72 hours. Left panels indicate position at which kymographs were registered (line), and middle panels show minimum intensity projections from the entire time series (Min. Proj). (d) Membrane ruffle quantification. (e) Ruffling speed quantification. (f) Leading edge kymography in control and iRFP670-EVL (green) expressing MCF7 cells (top and bottom rows, respectively), with eGFP-Lifeact (black) and MLC-mRuby2, before and after treatment with 75 μM ROCK inhibitor. Left panels are images from time-lapse series before and after treatment.
Figure 12:
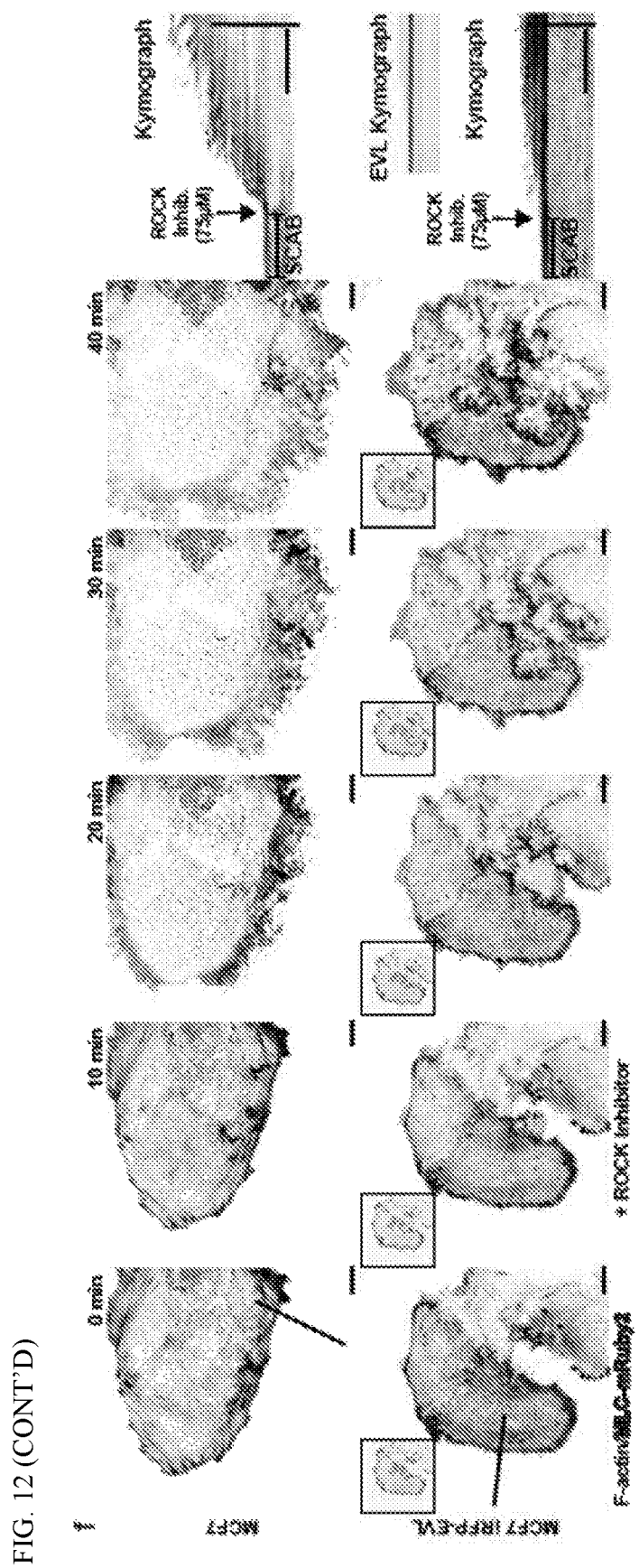

Remodeling of the actin cytoskeleton is controlled by a multitude of actin regulators whose differential expression in cancer leads to distinct architectures that impact invasion (Mouneimne, G. et al. Differential remodeling of actin cytoskeleton architecture by profilin isoforms leads to distinct effects on cell migration and invasion. Cancer Cell 22, 615-630 (2012)). To identify actin binding proteins that are transcriptionally regulated by ER, a targeted discovery approach was used by examining the differential expression of a curated list of 285 actin regulators in ER+ versus ER– tumors using 12 datasets (Curtis et al., supra; Ginestier, C. et al. Clinical Cancer Research 12, 4533-4544 (2006); Richardson, A. L. et al. Cancer Cell 9, 121-132 (2006); Lu, X. et al. Breast Cancer Res Treat 108, 191-201 (2008); Korde, L. A. et al. Breast Cancer Res Treat 119, 685-699 (2010); Gluck, S. et al. Breast Cancer Res Treat 132, 781-791 (2012); Kao, K.-J., et al. BMC Cancer 11, 143 (2011); Stickeler, E. et al. Oncol. Rep. 26, 1037-1045 (2011); Cancer Genome Atlas Network. Nature 490, 61-70 (2012); Esserman, L. J. et al. Breast Cancer Res Treat 132, 1049-1062 (2012); Miyake, T. et al. Cancer Sci. 103, 913-920 (2012)). The list of actin regulators was curated by first generating an extended list from the Gene Ontology (GO) Consortium using the broad search term 'actin cytoskeleton', and then refining it by limiting the selection to genes that specifically express actin binding proteins. In examining 12 independent microarray datasets, the Ena/VASP family member, EVL, was most differentially expressed in ER+ tumors, compared to ER– tumors (FIGS. 4a and 10a). This result was validated using the breast cancer TCGA RNA-seq dataset (FIG. 10b). Moreover, unsupervised clustering analysis of the RNA-seq data showed that EVL closely clustered with ESR1, the gene encoding ERα (FIG. 4b), and their expression exhibited the highest correlation index.

Strikingly, using ER ChIP-seq analysis, 2 high confidence ER peaks (defined in Methods) within the EVL gene and within 60 kb upstream of the transcription start site were found, indicating a direct regulation of EVL by E2-stimulated ER (FIG. 4c). Four of the high confidence peaks were further analyzed by ChIP-qPCR and two peaks showed significant enrichment in ER binding after E2 stimulation as compared to negative control targets (FIG. 4d). EVL mRNA expression was induced by E2 in both MCF7 and T47D cells and was suppressed by ER inhibition (FIGS. 4e and 10c). In addition, using immunofluorescence labeling, similar changes were observed in EVL protein levels in MCF7 cells after altering ER activity with the different treatments (FIGS. 4f and 4g). Together, these results demonstrate that EVL is a bona fide transcriptional target of ER. Notably, EVL is a characterized suppressor of breast cancer cell invasion (Bittner, supra), making it an ideal candidate for mediating the protective effects of ER against invasion.

Example 6

EVL Promotes ER-Mediated Actin Remodeling

EVL knock-down (KD), using validated EVL-targeting shRNA (Mouneimne, G. et al. Cancer Cell 22, 615-630 (2012)) (FIGS. 11a and b) rendered cells unresponsive to E2 by blocking the generation of SCABs and preventing the expected suppression of membrane motility dynamics by E2 treatment (FIGS. 5a and 5b and 11c-e). Conversely, overexpression of eGFP-EVL restored the generation of SCABs and suppressed protrusion under ER inhibition (FIGS. 5c and 5d and 12a-e). These results indicate that EVL is necessary and sufficient to generate ER mediated SCABs and promote the suppressive effects of ER on membrane motility dynamics.

Figure 5:
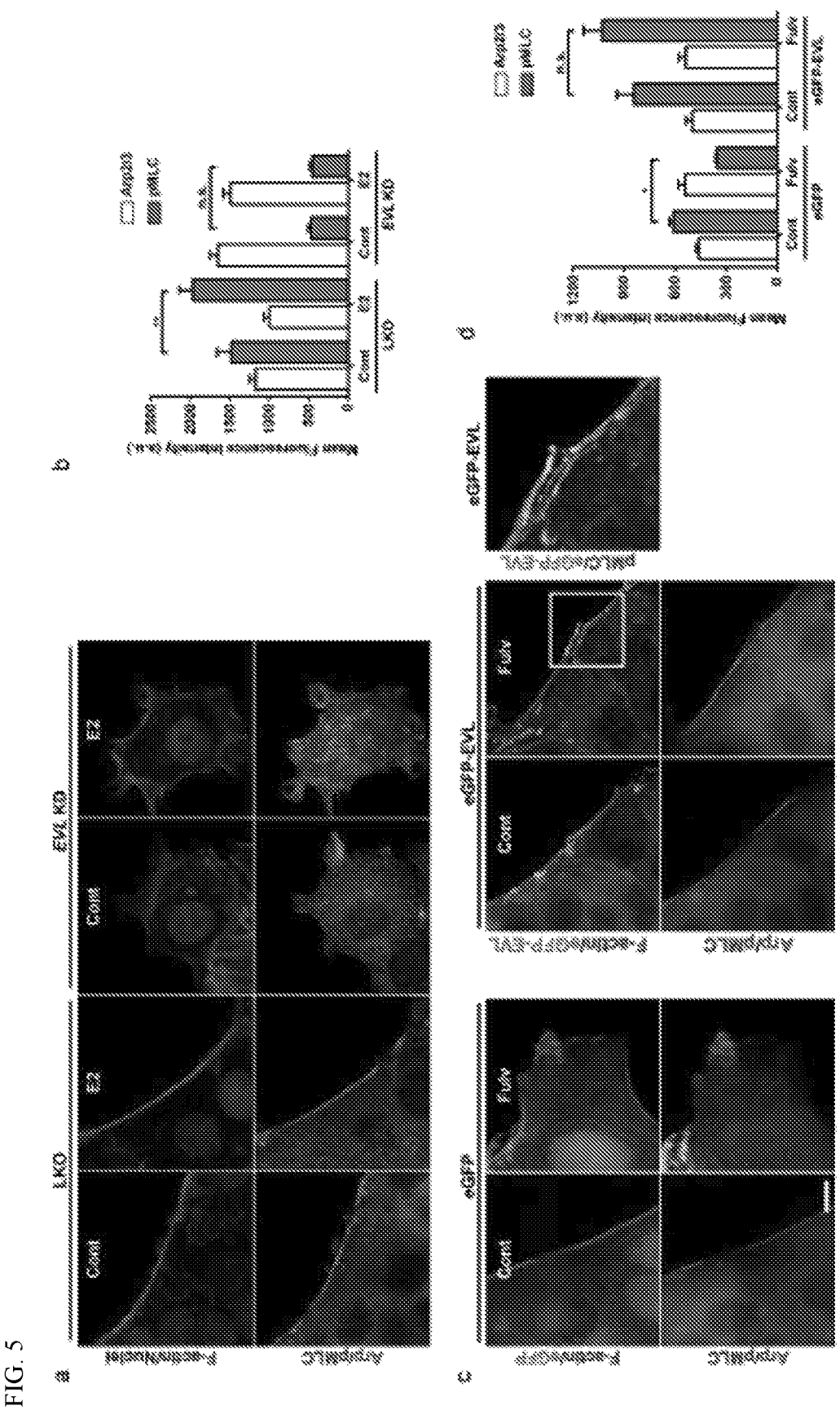
FIG. 5. EVL promotes ER-mediated actin remodeling. (a) Maximum intensity projection images of confocal z-series of MCF7 LKO and EVL KD cells treated with drug vehicle or E2 for 72 hours. (b) Volumetric quantification of Arp2/3 and pMLC levels at the leading edge. (c) Maximum intensity projections of confocal z-series of MCF7 eGFP and eGFP-EVL cells treated with drug vehicle or fulv for 72 hours. (d) Volumetric quantification of Arp2/3 and pMLC levels at the leading edge. (e) Analysis of EVL localization at SCABs by interferometric photoactivated localization microscopy (iPALM) in MCF7 cells expressing mEos2-EVL. Left panel is single and merged images of F-actin staining and mEos2-EVL with boxes indicating two ROIs. (f) Kymography analysis of protrusive activity and actin dynamics at the leading edge of control MCF7 cells expressing eGFP-Lifeact (black) and MLC-mRuby2, or in iRFP670-EVL expressing MCF7 cells (top and bottom rows, respectively), before and after treatment with 50 μM ROCK inhibitor. Left panels are images from TIRF microscopy time-lapse series before and after treatment.
Figure 5:
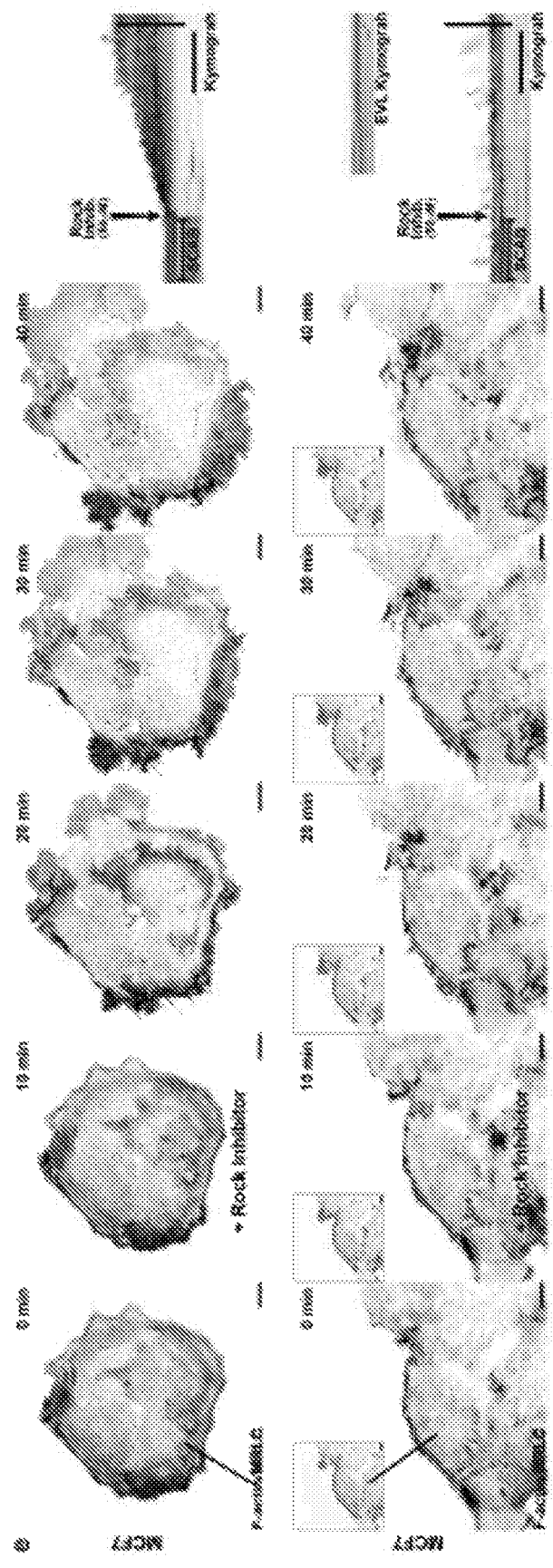
Figure 5:
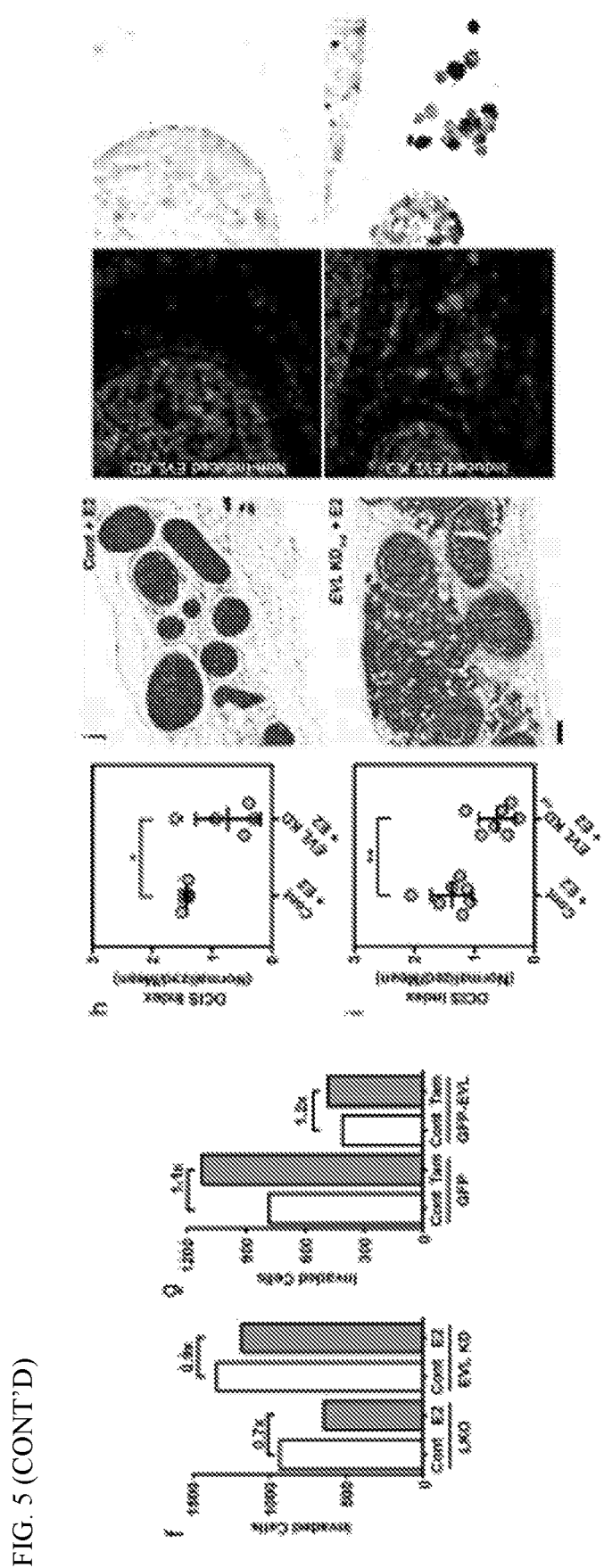
Figure 13:
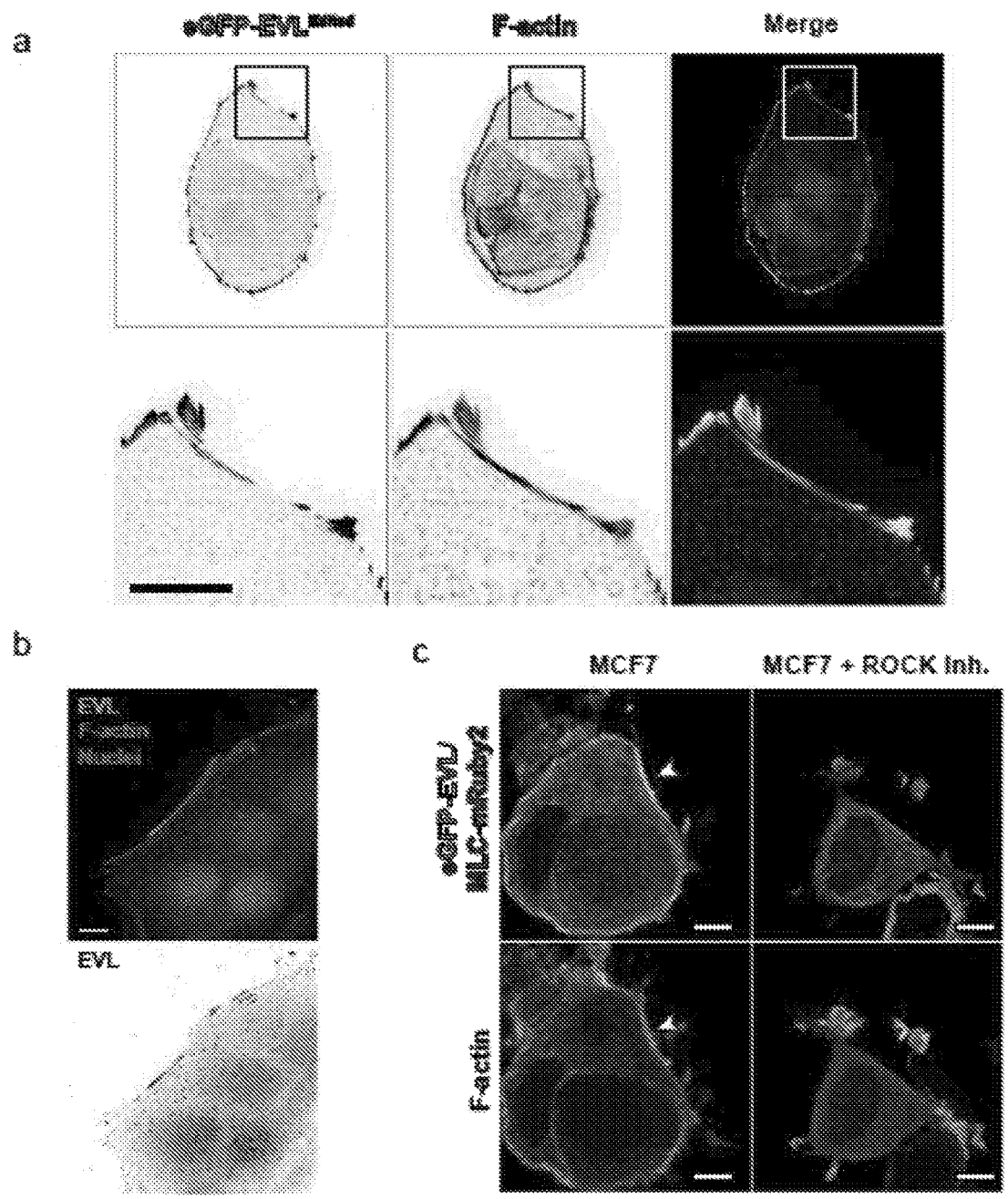
FIG. 13. (a) TIRF microscopy images of eGFP-EVL edited MCF7 cells. Lower panel are magnifications of boxed areas. (b) Immunolabeling of EVL in MCF7 cells. (c) Maximum projections of laser scanning confocal z-series of control and ROCK inhibitor-treated (25 μM) MCF7 cells expressing eGFP-EVL and MLC-mRuby2 embedded in collagen. Arrows indicate a SCAB. (d) Analysis of EVL localization at SCABs by iPALM of MCF7 cells stained for F-actin and expressing mEos2-EVL.
Figure 13:
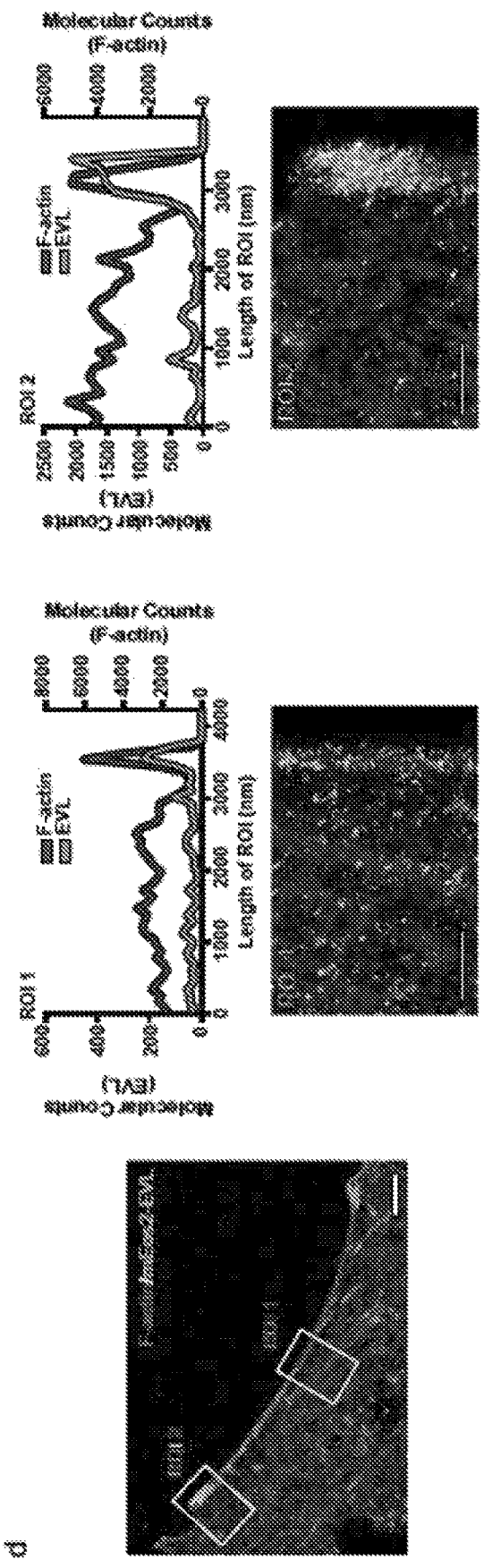

Both overexpressed eGFP-EVL and endogenous EVL (visualized in CRISPR-tagged eGFP-EVL cells and in EVL immunolabeled control cells) localized at SCABs (FIGS. 5c and 13 a and b). In addition, EVL was localized at SCABs in cell clusters embedded in 3D collagen matrix (FIG. 13c). To further analyze EVL localization at SCABs, mEos2-EVL and actin eere imaged using interferometric Photoactivated Localization Microscopy (iPALM), which allows for super-resolution molecular localization (within 10 nm) in the lateral and axial dimensions (Shtengel, G. et al. Interferometric fluorescent super-resolution microscopy resolves 3D cellular ultrastructure. Proc. Natl. Acad. Sci. U.S.A. 106, 3125-3130 (2009)). This analysis revealed that EVL enveloped the actin bundles in all dimensions at SCABs, as discerned in orthogonal projections of cross sectional segments taken across different regions of the SCABs (FIG. 5e). Moreover, EVL was highly enriched at the tips of SCABs, which extended into the focal adhesions; notably, at focal adhesions EVL localization was predominantly basal to actin (FIGS. 5e and 13d).

While inhibition of contractility dissolved SCABs and increased protrusive activity in control cells, EVL-overexpressing cells exhibited a higher threshold of sensitivity and their SCABs were more resistant to contractility inhibitors (FIGS. 5f and 13f). This indicates that increased EVL expression not only leads to the enrichment of SCABs but

Example 7

Figure 6:
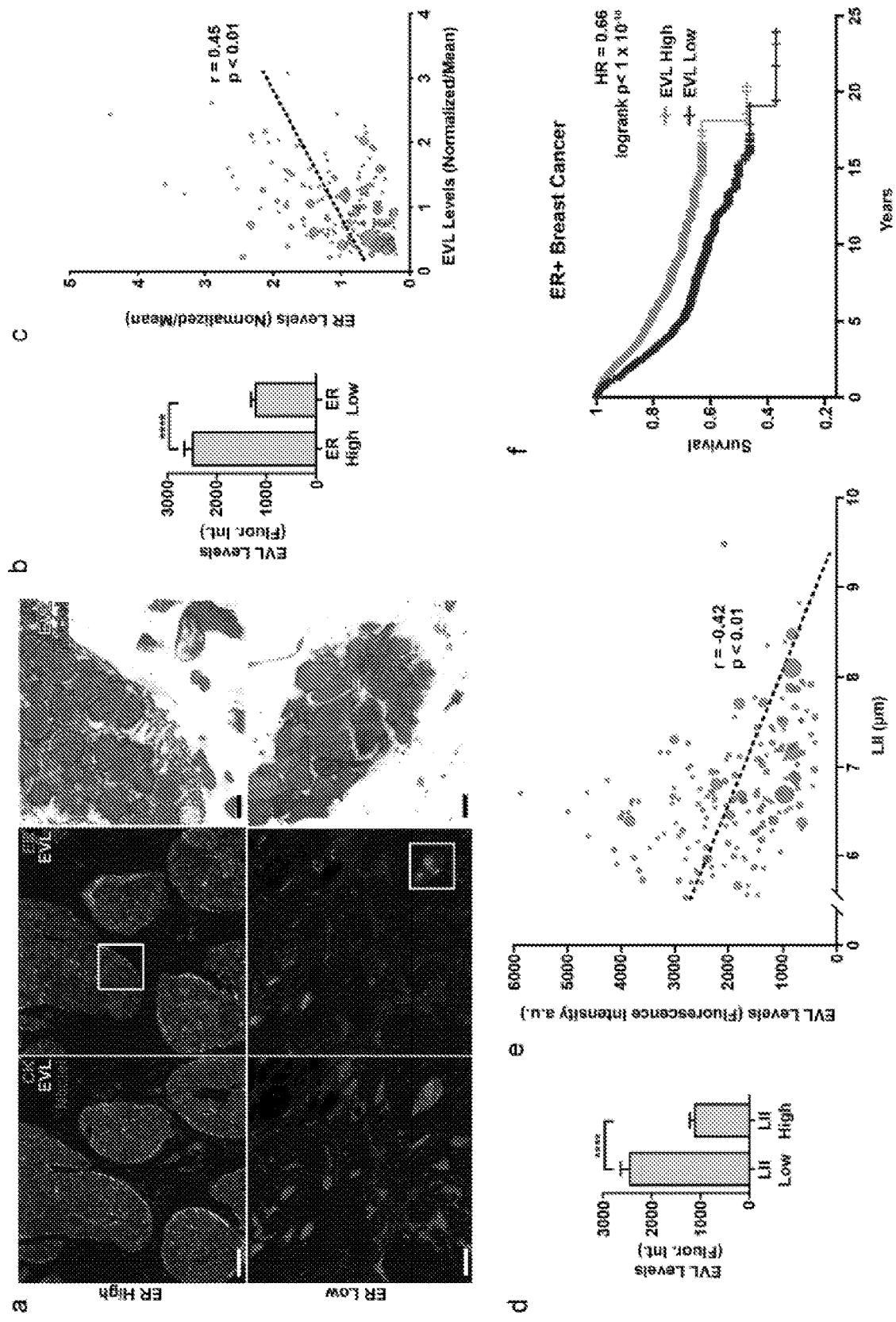
FIG. 6. EVL suppresses invasive activity of breast cancer cells and is associated with low dissemination in breast tumors. Quantification of Invasion in Vitro: (a) Representative luminal B breast tumors with high (top panels) or low (bottom panels) ER expression. Left panels show merged images of cytokeratin and EVL immunolabeling and middle panels of ER and EVL immunolabeling. (b) Quantification of EVL levels in ER Low ($1^{st}$ quartile) and ER High ($3^{rd}$ quartile) tumors (mean+s.e.m. **$p<0.0001$). (c) scatter plot of ER and EVL levels. (d) Quantification of EVL levels in LII Low (≤7 μm) and LII High (>9 μm) tumors (mean+s.e.m. **$p<0.0001$). (e) Scatter plot of EVL levels and LII. (f) survival of subjects with ER+ breast cancer with EVL high and EVL low levels.
Figure 14:
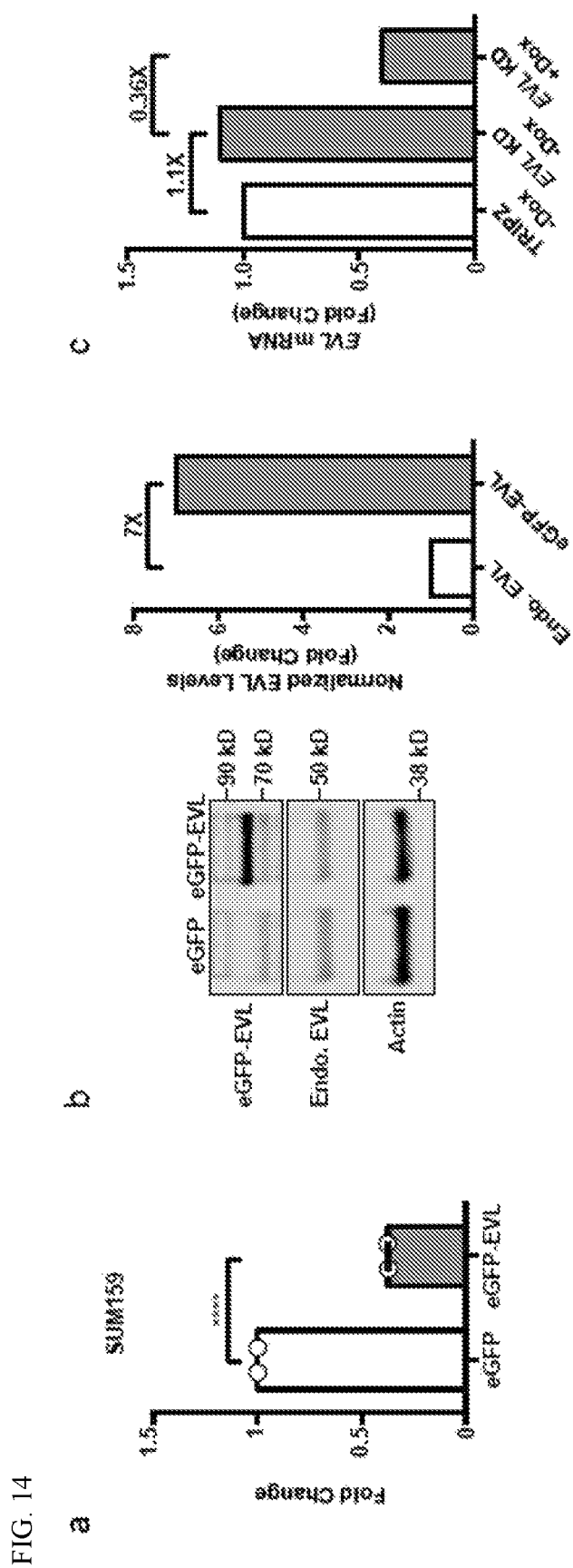
FIG. 14. (a) Quantification of in vitro invasion of control and eGFP-EVL overexpressing SUM159 cells. (b) Left panel. Western blot of eGFP and eGFP-EVL SUM159 cell lysates showing EVL levels and actin loading control. Right panel. Quantification of western blot showing fold change in EVL levels relative to endogenous EVL, normalized to actin. (c) qPCR of EVL mRNA in control TRIPZ MCF7 cells and inducible EVL KD with or without doxycycline (dox) induction. Brackets show fold change. (d) Representative images from six patient samples showing SCABs in tumors, as demarcated by EVL immunofluorescence labeling. (e) Kaplan-Meier plot showing survival of luminal B breast cancer patients clustered by EVL expression (split by at median).
Figure 14:
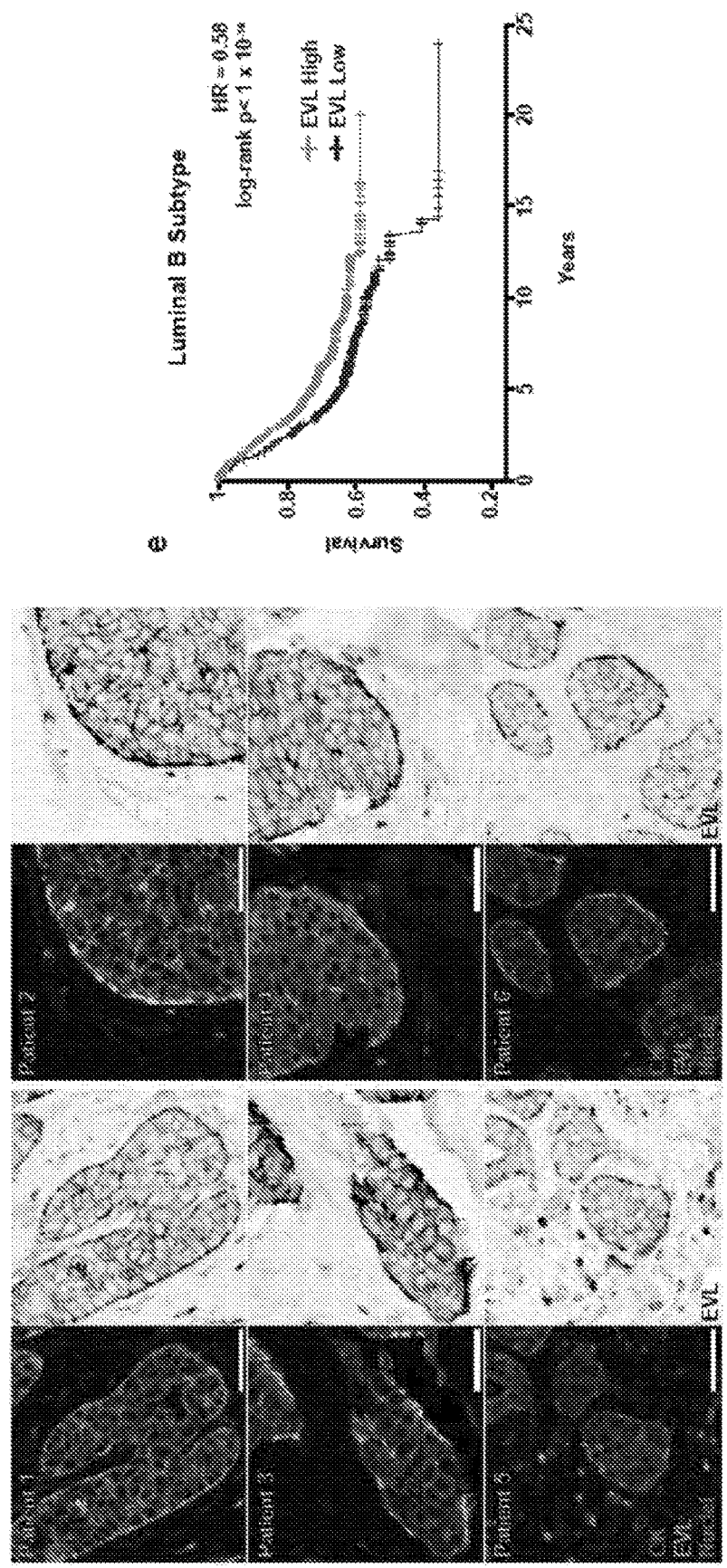

EVL Suppresses Invasive Activity of Breast Cancer Cells and is Associated with Low Local Invasion in Breast Tumors Importantly, EVL overexpression attenuated the increase in invasion induced by ER inhibition, whereas EVL KD reversed the suppressive effects of E2 on invasion (FIGS. 6a and 6b). Moreover, EVL overexpression was sufficient to suppress invasion in ER negative breast cancer SUM159 cells (FIG. 14a). Together, these data indicate that EVL is necessary and sufficient to promote the E2-mediated suppression of invasion in vitro.

To extend these results in vivo, the role of EVL in ER+ breast cancer progression was examined using an intraductal MCF7 xenograft model (Sflomos, G. et al. A Preclinical Model for ERα-Positive Breast Cancer Points to the Epithelial Microenvironment as Determinant of Luminal Phenotype and Hormone Response. Cancer Cell 29, 407-422 (2016)). This model was used because it generates non-invasive Ductal Carcinoma In Situ (DCIS) structures and maintains luminal differentiation, as opposed to fat-pad implantation, which induces mesenchymal differentiation (Sflomos, G. et al., supra). Assessment of the intraductal tumors using a DCIS index (see Methods) showed that under E2 treatment, EVL KD constitutive (FIGS. 6c and 11a) and induced (FIGS. 6d and 6e and 14b) reduced the DCIS index and increased invasion compared to control. Consistent with the in vitro invasion data, these results show that EVL is necessary for mediating the suppression of invasion by ER in vivo.

Furthermore, analysis of immunofluorescence labeling of EVL and ER in luminal B tumor samples from TMA #2 resulted in the following findings: first, EVL immunolabeling demonstrated the presence of SCABs in tumors (FIG. 14c); second, expression analysis revealed that the levels of EVL and ER are positively correlated, to the extent that, within tumors exhibiting heterogeneity in ER expression, EVL expression changes with that of ER at the single-cell level (FIG. 6f-h); and third, tumors expressing low EVL exhibited high LII (FIGS. 6i and 6j) and more distant dissemination (EVL was ~30% less in tumors with LN>3, $p=3 \times 10^{-5}$). Importantly, survival analysis showed low EVL expression was associated with poor outcome in ER+ breast cancer in general, and in the luminal B subtype in particular (FIGS. 6k and 14d).

Example 8

Figure 7:
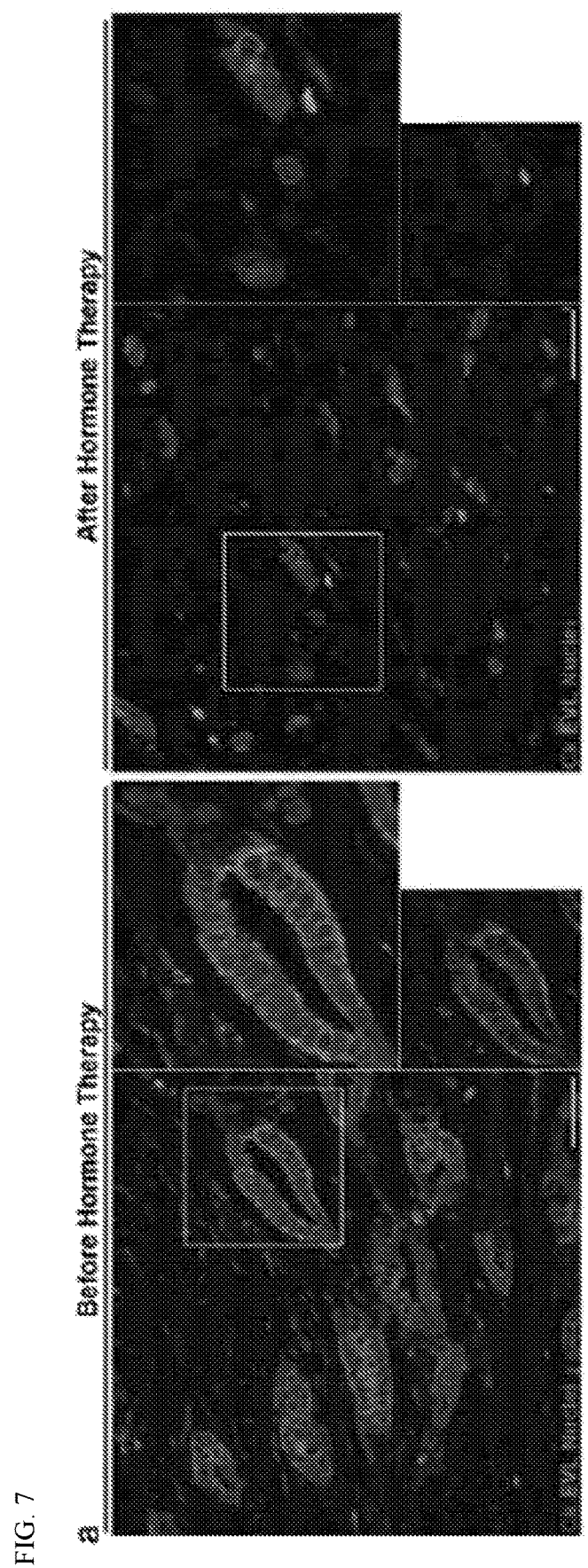
FIG. 7. Anti-estrogenic hormone therapy is associated with decreased EVL expression and increased local invasion in tumors post treatment. (a) Representative images of ER+ breast tumor before (left panel) and after (right panel) neo-adjuvant hormone therapy, immunolabeled for human cytokeratin, EVL and nuclei. (b) Quantification of EVL levels before and after hormone therapy. (c) Quantification of Local Invasion Index (LII) before and after therapy. (d) Histograms showing percentage of cells within different LII bins, before and after therapy.
Figure 7:
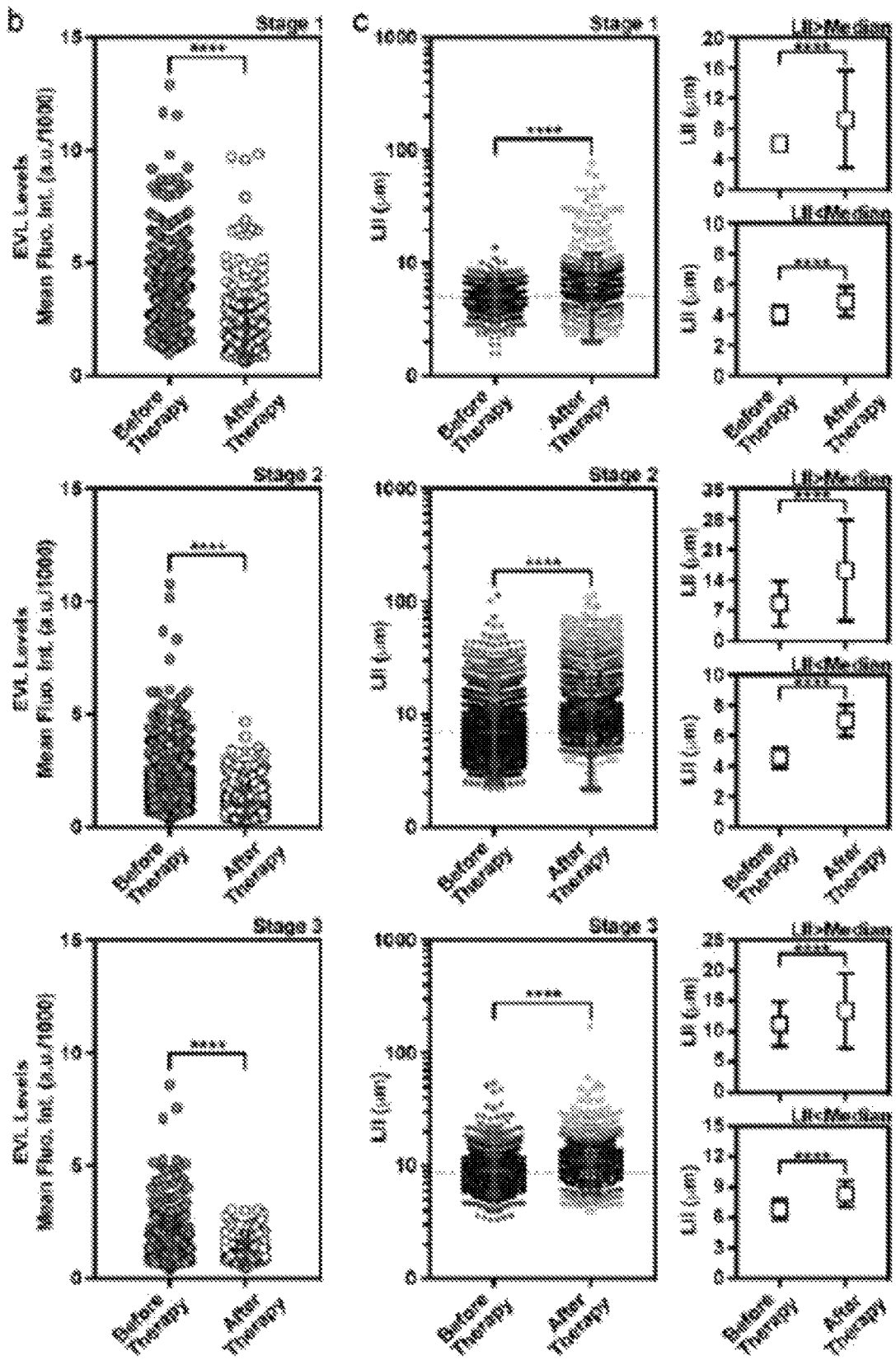
Figure 7:
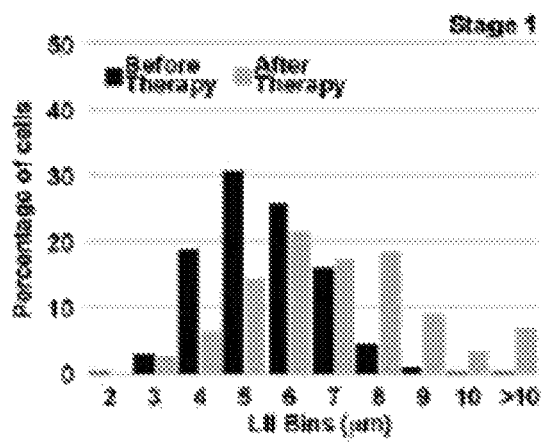
Figure 7:
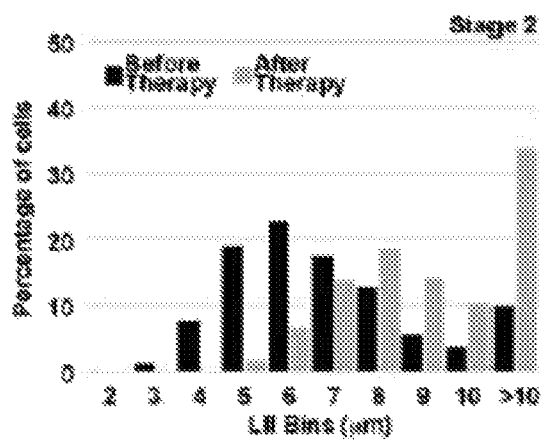
Figure 7:
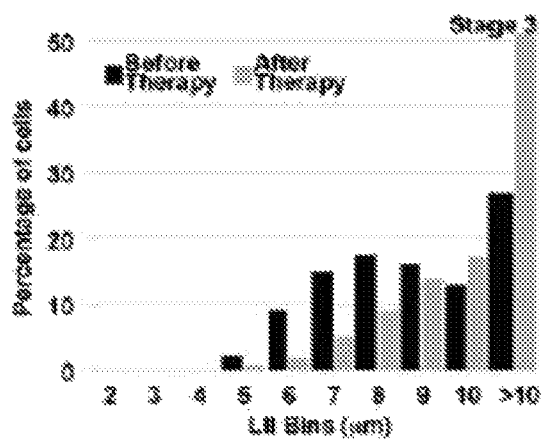

Anti-Estrogenic Hormone Therapy is Associated with Decreased EVL Expression and Increased Local Invasion in Tumors Post Treatment The effects of anti-estrogenic hormone therapy on EVL expression and invasion was examined in ER+ breast cancer. Tumor samples were obtained from patients who were treated with neo-adjuvant hormone therapy, and they were compared to matching biopsy samples taken from the same tumors before therapy. Invasion and EVL expression were examined at the single cell level in a large population of tumor cells from three sets of before- and after-therapy tissue samples. Samples were collected from patients in stages 1, 2, and 3, thus covering a range of invasive behaviors from different stages of progression. Importantly, the single-cell analysis approach allowed us to capture intratumoral heterogeneity and examine changes in population dynamics in response to treatment. EVL labeling revealed that prolonged anti-estrogenic therapy led to a dramatic decrease in EVL expression, which was associated with a decrease in ER (FIGS. 7a and 7b). Analysis of local invasion (LII) showed that tumors became more invasive after treatment (FIGS. 7c and 7d). Particularly, the portion of highly invasive cells (LII high) increased after treatment, especially in stage 1 and stage 2 tumors, which exhibited a lower number of invasive cells prior to treatment (FIGS. 7c and 7d). These data indicate that anti-estrogenic hormone therapy, prescribed for these patients as neo-adjuvant therapy to curb further growth of the tumors, potentially enhanced invasion with a marked decrease in EVL expression.

All publications, patents, patent applications and accession numbers mentioned in the above specification are herein incorporated by reference in their entirety. Although the invention has been described in connection with specific embodiments, it should be understood that the invention as claimed should not be unduly limited to such specific embodiments. Indeed, various modifications and variations of the described compositions and methods of the invention will be apparent to those of ordinary skill in the art and are intended to be within the scope of the following claims.

We claim:

1. A method of treating breast cancer in a subject, comprising:
    a) assaying a sample comprising breast cancer cells from a subject diagnosed with breast cancer for the level of expression of Enah/Vasp-Like gene (EVL);
    b) assaying said sample for the level of expression of estrogen receptor;
    c) identifying said breast cancer cells as having a level of expression of EVL lower than a reference level, wherein said reference level is the level of EVL in estrogen receptor negative breast cancer cells;
    d) identifying said breast cancer cells as estrogen receptor positive; and
    e) administering anti-estrogen adjuvant therapy to the subject identified as having estrogen receptor positive breast cancer cells and a level of expression of EVL lower than said reference level.

2. The method of claim 1, wherein said anti-estrogen therapy is an estrogen receptor antagonist or an aromatase inhibitor.

3. The method of claim 1, wherein said anti-estrogen therapy is selected from the group consisting of tamoxifen, fulvestrant, toremifene, letrozole, anastrozole, and exemestane.

4. The method of claim 1, wherein said method further comprises administering chemotherapy.

5. The method of claim 1, wherein following administration of said anti-estrogen therapy, estrogen therapy is administered to said subject.

6. The method of claim 5, wherein said subject does not exhibit a response to said anti-estrogen therapy.

7. The method of claim 5, wherein said estrogen therapy promotes the generation of Suppressive Cortical Actin Bundles (SCABs).

* * * * *